(12) United States Patent
Obst et al.

(10) Patent No.: US 11,207,097 B2
(45) Date of Patent: Dec. 28, 2021

(54) FLUID MANAGEMENT DEVICE FOR MEDICAL TUBES AND DRAINAGE INCISIONS

(71) Applicants: Andrew Thomas Obst, Scandia, MN (US); Maryanne Ruth Obst, Scandia, MN (US)

(72) Inventors: Andrew Thomas Obst, Scandia, MN (US); Maryanne Ruth Obst, Scandia, MN (US)

(*) Notice: Subject to any disclaimer, the term of this patent is extended or adjusted under 35 U.S.C. 154(b) by 54 days.

(21) Appl. No.: 16/275,029

(22) Filed: Feb. 13, 2019

(65) Prior Publication Data
US 2020/0253633 A1    Aug. 13, 2020

(51) Int. Cl.
*A61J 15/00* (2006.01)
*A61B 17/34* (2006.01)
(Continued)

(52) U.S. Cl.
CPC .......... *A61B 17/3417* (2013.01); *A61F 5/445* (2013.01); *A61J 15/0015* (2013.01); *A61J 15/0034* (2013.01); *A61M 27/00* (2013.01); *A61M 39/0247* (2013.01); *A61B 2017/3419* (2013.01); *A61B 2090/037* (2016.02);
(Continued)

(58) Field of Classification Search
CPC ....... A61B 2017/3419; A61B 2090/037; A61F 2005/4483; A61F 5/445; A61J 15/0034; A61M 2039/0276; A61M 39/0247
See application file for complete search history.

(56) References Cited

U.S. PATENT DOCUMENTS

| 3,398,744 A | 8/1968 | Hooper et al. |
| 5,015,244 A | 5/1991 | Cross |

(Continued)

FOREIGN PATENT DOCUMENTS

| EP | 3406275 A1 | 11/2018 |
| WO | WO-2004084778 A2 | 10/2004 |

(Continued)

OTHER PUBLICATIONS

Communication dated Jan. 16, 2020 for EP Application No. 15 857 923.5, 5 pages.
(Continued)

*Primary Examiner* — Deanna K Hall
(74) *Attorney, Agent, or Firm* — Patterson Thuente Pedersen, P.A.

(57) ABSTRACT

A device, system, kit, and method for managing the passage of fluid through an opening in the body of a patient that includes a fluid-containment receptacle including a collapsible sidewall, the fluid-containment receptacle having a first receptacle opening and a second receptacle opening positioned at opposite ends of the sidewall, the fluid-containment receptacle. The device also including a first flange extending radially outward from the sidewall and positioned at or adjacent to the first receptacle opening and a second flange extending radially outward from the sidewall at or adjacent to the second receptacle opening. The device is configured to be applied to the opening in the body of the patient such that the first opening and the first flange contact the body of the patient and form a fluid barrier around the opening.

18 Claims, 15 Drawing Sheets

(51) Int. Cl.

| | | |
|---|---|---|
| *A61F 5/445* | (2006.01) | |
| *A61M 27/00* | (2006.01) | |
| *A61M 39/02* | (2006.01) | |
| A61B 90/00 | (2016.01) | |
| A61F 5/448 | (2006.01) | |

(52) U.S. Cl.
CPC .............. *A61F 2005/4483* (2013.01); *A61M 2039/027* (2013.01); *A61M 2039/0276* (2013.01)

(56) References Cited

U.S. PATENT DOCUMENTS

| | | | |
|---|---|---|---|
| 5,429,626 A | 7/1995 | Fenton | |
| 5,636,643 A | 6/1997 | Argenta et al. | |
| 5,738,661 A | 4/1998 | Larice | |
| 6,099,508 A | 8/2000 | Bousquet | |
| 6,709,421 B1 | 3/2004 | Falconer | |
| 6,765,122 B1 | 7/2004 | Stout | |
| 7,147,627 B2 | 12/2006 | Kim et al. | |
| 7,708,724 B2 | 5/2010 | Weston | |
| 8,167,857 B2 | 5/2012 | James | |
| 8,409,157 B2 | 4/2013 | Haggstrom et al. | |
| 8,529,526 B2 | 9/2013 | Wilkes et al. | |
| 8,758,314 B2 | 6/2014 | Hall et al. | |
| 8,915,894 B1 | 12/2014 | Lonky et al. | |
| 9,078,990 B1 | 7/2015 | Obst et al. | |
| 9,265,665 B2 | 2/2016 | Robinson et al. | |
| 9,782,328 B2 | 10/2017 | Gutwein et al. | |
| 10,182,947 B2 | 1/2019 | Hu et al. | |
| 2007/0191794 A1 | 8/2007 | Cline et al. | |
| 2008/0161778 A1 | 7/2008 | Steward | |
| 2008/0269700 A1 | 10/2008 | O'Toole et al. | |
| 2008/0287892 A1 | 11/2008 | Khan et al. | |
| 2008/0319397 A1 | 12/2008 | Macaluso | |
| 2009/0131893 A1 | 5/2009 | Priest et al. | |
| 2009/0192467 A1 | 7/2009 | Hansen et al. | |
| 2009/0209917 A1 | 8/2009 | Tanaka et al. | |
| 2010/0145293 A1 | 6/2010 | Verhaalen | |
| 2010/0262095 A1 | 10/2010 | Hall | |
| 2010/0280489 A1 | 11/2010 | Nishtala et al. | |
| 2010/0312192 A1 | 12/2010 | Fitzgerald et al. | |
| 2011/0040269 A1 | 2/2011 | Cline | |
| 2011/0137270 A1 | 6/2011 | Hu et al. | |
| 2012/0029450 A1 | 2/2012 | Grum-Schwensen | |
| 2012/0130187 A1 | 5/2012 | Okoniewski | |
| 2012/0232505 A1* | 9/2012 | Eskaros .................. A61F 5/445 604/335 |
| 2014/0148771 A1 | 5/2014 | Luce | |
| 2014/0207027 A1 | 7/2014 | Navia et al. | |
| 2014/0309604 A1 | 10/2014 | Paratore | |
| 2014/0324002 A1 | 10/2014 | Luce | |
| 2015/0100045 A1 | 4/2015 | Allen et al. | |
| 2016/0120687 A1 | 5/2016 | Obst et al. | |
| 2016/0287428 A1* | 10/2016 | Eggert .................. A61F 5/445 |
| 2017/0361069 A1 | 12/2017 | Gazzani Romolo et al. | |
| 2017/0367871 A1 | 12/2017 | Dinakara et al. | |
| 2019/0046698 A1 | 2/2019 | Loske | |
| 2020/0405523 A1 | 12/2020 | Obst et al. | |

FOREIGN PATENT DOCUMENTS

| | | |
|---|---|---|
| WO | WO 2009/049232 A1 | 4/2009 |
| WO | WO 2010/075032 A2 | 7/2010 |
| WO | WO-2011015203 A1 | 2/2011 |
| WO | WO-2011031822 A1 | 3/2011 |
| WO | WO 2011/138727 A1 | 11/2011 |
| WO | WO 2014/140606 A1 | 9/2014 |

OTHER PUBLICATIONS

Aguila III D.J., et al., "The Stool Shield: A Novel Approach to the Colo-Atmospheric Fistula," Journal of the American College of Surgeons, Sep. 2011, vol. 213 (3), pp. e17-e20.

Byrnes M.C., et al., "A Novel Technique to Skin Graft Abdominal Wall Wounds Surrounding Enterocutaneous Fistulas," Surgical Infections, vol. 11 (6), Apr. 18-20, 2010, pp. 505-510.

Extended European Search Report for Application No. 15857923.5, dated May 2, 2018, 9 pages.

Goverman J., et al., "The "Fistula VAC," a Technique for Management of Enterocutaneous Fistulae Arising within the Open Abdomen: Report of 5 Cases," The Journal of Trauma Injury, Infection, and Critical Care, Feb. 2006, vol. 60 (2), pp. 428-431.

International Preliminary Report on Patentability for Application No. PCT/US2015/058740, dated May 18, 2017, 12 pages.

International Search Report and Written Opinion for Application No. PCT/US2015/058740, dated Feb. 3, 2016, 16 pages.

Stremitzer S., et al., "Successful Bridging Treatment and Healing of Enteric Fistulae by Vacuum-Assisted Closure (VAC) Therapy and Targeted Drainage in Patients with Open Abdomen," International Journal of Colorectal Disease, vol. 26, Jan. 2011, pp. 661-666.

Application and File history for U.S. Appl. No. 13/750,154, filed Jan. 25, 2013.

Application and File history for U.S. Appl. No. 14/931,204, filed Nov. 3, 2015.

Search Report dated Jul. 14, 2020 for EP Application No. 20157187.4, 11 pages.

Application and File history for U.S. Appl. No. 16/453,315, filed Jun. 26, 2019.

* cited by examiner

FLUID MANAGEMENT DEVICE FOR MEDICAL TUBES AND DRAINAGE INCISIONS

TECHNICAL FIELD

This disclosure relates to medical devices for use with bodily fluid management systems, drainage incisions, and the like.

BACKGROUND

Leakage of bodily fluids such as gastric, fecal, exudate, or other fluids around medical tubes (e.g., drainage tubes, feeding tubes, and the like) or drainage incisions is a common occurrence in several medical procedures. Fluid leakage can occur around both natural orifices such as the anus and vagina as well as around surgical openings which may or may not have medical tubes placed in such openings. In some instances, the leaked fluid may cause irritation, infection, reduced healing times, or general discomfort to the patient. Management of such fluid leakage can present many challenges for the patients and healthcare professionals.

Examples of medical tubes conventionally used with fluid management systems may include, for example, fecal management tubes, gastric feeding tubes, and drainage tubes for surgical incisions. Fecal management systems may be inserted through the rectum into the colon to funnel liquid stool into the fecal management tube that passes through the anus and outside the body. Gastric feeding tubes, also referred to as Percutaneous Endoscopic Gastrostomy (PEG) tubes, may be inserted through an incision in the abdominal wall and terminate in the stomach or small bowel so that nutritional fluids can be put directly into the body. Drainage incisions are created by clinicians to prevent fluid from collecting in a wound and to remove the excess blood, infectious material, and fluid from under the skin, the chest cavity, the abdomen and other areas of the body.

Example fluid management devices and systems are described in U.S. patent publications 2010/0280489 to Nishtala; U.S. Pat. No. 7,147,627 to Kim; U.S. Pat. No. 9,782,328 to Gutwein; 6,765,122 to Stout; and U.S. Pat. No. 5,738,661 to Larice that may be used to control the entry or exit of fluids into the body of a patient. Such systems, however, may experience fluid leakage around medical tubes, drainage incisions, or the like which can lead to irritation, infection, or increased healing durations. Even with proper placement of such fluid management systems, fluid leakage can still occur. There remains a need for improved devices and systems for managing fluid leakage from patients.

SUMMARY

This disclosure describes medical devices that may be used to manage fluid leakage from openings in the body of a patient. In some examples, the fluid management devices described herein may be used with fluid management systems to help stabilize medical tubes and/or drainage incisions and help reduce and redirect fluid leakage through a target opening. As described further below, the disclosed devices may be used alone or in combination with medical tubes, wound dressings, or other fluid management appliances to address one or more problems that are commonly observed with conventional fluid management systems.

In some examples, the disclosure describes a device for managing the passage of fluid through an opening in the body of a patient. The device includes a fluid-containment receptacle that includes a collapsible sidewall that extends along a longitudinal axis. The fluid-containment receptacle includes a first receptacle opening and a second receptacle opening positioned at opposite ends of the sidewall and the fluid-containment receptacle is configured to collapse from a first height to a second height less than the first height when subject to axial force applied to the device along the longitudinal axis. The device further includes a first flange extending radially outward from the sidewall and positioned at or adjacent to the first receptacle opening and a second flange extending radially outward from the sidewall at or adjacent to the second receptacle opening, where the device is configured to be applied to the opening in the body of the patient such that the first opening and the first flange contact the body of the patient and form a fluid barrier against the body of the patient.

In some examples, the disclosure describes a bodily fluid management system that includes a medical tube for introducing or removing a fluid through an opening in a body of a patient and a fluid management device configured to be received over the medical tube and form a fluid barrier against the body of the patient. The fluid management device includes a fluid-containment receptacle including a collapsible sidewall that extends along a longitudinal axis, in which the fluid-containment receptacle includes a first receptacle opening and a second receptacle opening positioned at opposite ends of the sidewall and the fluid-containment receptacle is configured to collapse from a first height to a second height less than the first height when subject to axial force applied to the device along the longitudinal axis. The device further includes a first flange extending radially outward from the sidewall and positioned at or adjacent to the first receptacle opening and a second flange extending radially outward from the sidewall at or adjacent to the second receptacle opening, where the device is configured to be applied to the opening in the body of the patient such that the first opening and the first flange contact the body of the patient and form a fluid barrier against the body of the patient.

The above summary is not intended to describe each illustrated embodiment or every implementation of the subject matter hereof. The figures and the detailed description that follow more particularly exemplify various examples. Other features, objects, and advantages will be apparent from the description and drawings, and from the claims.

BRIEF DESCRIPTION OF THE DRAWINGS

Subject matter hereof may be more completely understood in consideration of the following detailed description of the various examples in connection with the accompanying figures.

FIGS. 2A-2L illustrate various cross-sectional and aerial views of optional placements and constructions for tube retainers that may be used with the device of FIGS. 1A-1E, in which:

FIG. 2A is a side cross-sectional view of a device according to an embodiment;

FIG. 2B is a top view of the embodiment of FIG. 2A;

FIG. 2C is a side cross-sectional view of a device according to another embodiment;

FIG. 2D is a top view of the embodiment of FIG. 2C;

FIG. 2E is a side cross-sectional view of a device according to another embodiment;

FIG. 2F is a top view of the embodiment of FIG. 2E;

FIG. 2G is a side cross-sectional view of a device according to another embodiment;

FIG. 2H is a top view of the embodiment of FIG. 2G;

FIG. 2I is a side cross-sectional view of a device according to another embodiment;

FIG. 2J is a top view of the embodiment of FIG. 2I;

FIG. 2K is a side cross-sectional view of a device according to another embodiment; and FIG. 2L is a top view of the embodiment of FIG. 2K.

FIGS. 3A-3H illustrate various cross-sectional and aerial views of another example device that includes a tube retention sleeve that may be used help secure the device to a medical tube, in which:

FIG. 3A is a side cross-sectional view of a device according to an embodiment;

FIG. 3B is a top view of the embodiment of FIG. 3A;

FIG. 3C is a side cross-sectional view of a device according to another embodiment;

FIG. 3D is a top view of the embodiment of FIG. 3C;

FIG. 3E is a side cross-sectional view of a device according to another embodiment;

FIG. 3F is a top view of the embodiment of FIG. 3E;

FIG. 3G is a side cross-sectional view of a device according to another embodiment; and FIG. 3H is a top view of the embodiment of FIG. 3G.

FIGS. 4A-4D illustrate various cross-sectional and aerial views of example configurations for the fluid-containtainment receptacle of the device of FIGS. 1A-1E, in which:

FIG. 4A is a side cross-sectional view of a device according to an embodiment;

FIG. 4B is a top view of the embodiment of FIG. 3A;

FIG. 4C is a side cross-sectional view of a device according to another embodiment; and FIG. 4D is a top view of the embodiment of FIG. 4C.

FIGS. 5A and 5B are cross-sectional views of example devices showing different example constructions for the fluid-containment receptacle that may be used with the device of FIGS. 1A-1E, in which:

FIG. 5A is a side cross-sectional view of a device according to an embodiment; and FIG. 5B is a side cross-sectional view of a device according to another embodiment.

FIGS. 6A-6D are cross-sectional views of example devices showing different example constructions for the skirt and first flange which may be used with the device of FIGS. 1A-1E to help establish a fluid barrier against the device and body of a patient, in which:

FIG. 6A is a side cross-sectional view of a device according to an embodiment;

FIG. 6B is a side cross-sectional view of a device according to another embodiment;

FIG. 6C is a side cross-sectional view of a device according to another embodiment; and FIG. 6D is a side cross-sectional view of a device according to another embodiment.

FIGS. 11A-11E are various side views of the example devices described herein being used in combination with wound dressing drapes or other wound care devices, in which:

FIG. 11A is a side view of a wound care device according to an embodiment and adhered to a patient over an opening with an adhesive wound drape placed on an upper flange around a receptacle opening of the device;

FIG. 11B is a side view of the wound care device according to FIG. 11A and including a negative pressure wound care dressing;

FIG. 11C is a side view of a wound care device according to an embodiment and adhered to a patient over an opening with adhesive placed below an lower flange around the receptacle opening of the device; and FIG. 11D is a side view of the wound care device according to an embodiment and adhered to a patient over an opening with an adhesive wound drape placed on the flange around the receptacle opening of the device.

FIGS. 12A-12C are various side views of the example devices described herein installed subcutaneously in the opening of a patient and being used in combination with wound dressing drapes or other wound care devices, in which:

FIG. 12A is a side elevational view of the device installed subcutaneously with an adhesive wound drape according to an embodiment;

FIG. 12B is a side elevational view of the device installed subcutaneously an adhesive wound drape and negative pressure wound care dressing according to another embodiment; and FIG. 12C is a side elevational view of the device installed subcutaneously with an adhesive between flanges according to another embodiment.

FIGS. 13A and 13B are cross-sectional views of the example devices described herein being used in combination with other optional fluid management devices, in which:

FIG. 13A is a side cross-sectional view of a device according to an embodiment used in combination with medical tube and a suction tube; and FIG. 13B is a side cross-sectional view of a device according to an embodiment in combination with absorbent dressing.

Figure 1A:
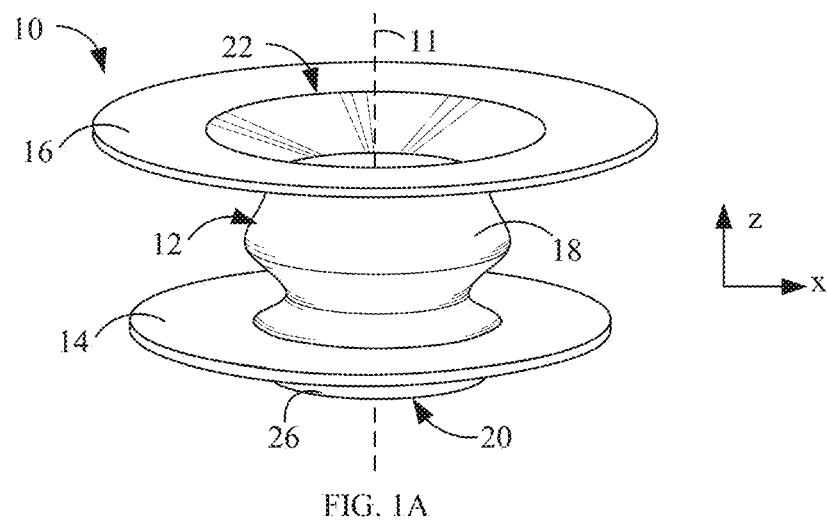
FIG. 1A is a front perspective view of an example fluid management device which may be used to control fluid leakage from an opening (e.g., wound, incision, or orifice) in the body of a patient.

While various examples are amenable to various modifications and alternative forms, specifics thereof have been shown by way of example in the drawings and will be described in detail. It should be understood, however, that the intention is not to limit the claimed inventions to a particular embodiment described.

DETAILED DESCRIPTION OF THE DRAWINGS

The present disclosure describes various examples of fluid management devices that may be used in medical related procedures to help control and manage bodily fluids (e.g., wound exudate, gastric fluid, stool, and the like). As described in further detail below, the devices described herein may be used alone or in combination with such fluid management systems to address one or more of the problems outlined above. By way of example, the devices disclosed herein may be used to at least one of create a fluid barrier (e.g., a seal) between the device and the skin/opening of the patient, redirect any fluid leakage away from the skin of the patient, radially and axially stabilized and isolate the placement of a medical tube, reduce the quantity of fluid that leaks around such medical tubes, or help maintain the opening of a drainage incision. The fluid barrier may substantially or completely prevent the passage of fluid leaking through the points of contact between the device and the body of the patient.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Figure 1B:
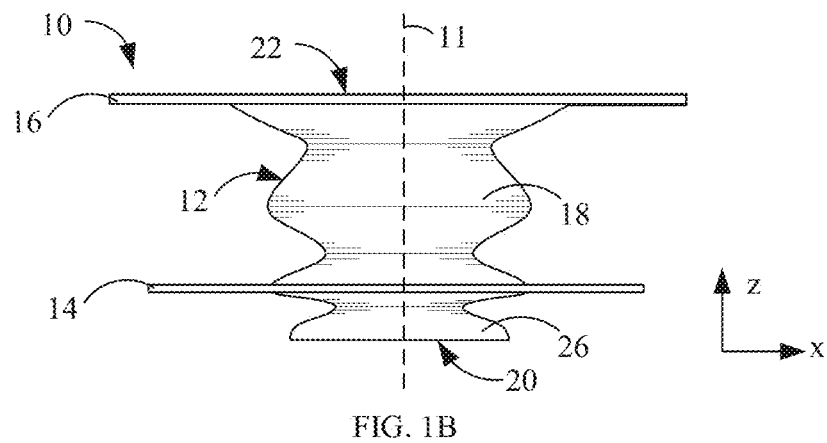
FIG. 1B is a side elevational view of the device of FIG. 1A.
Figure 1C:
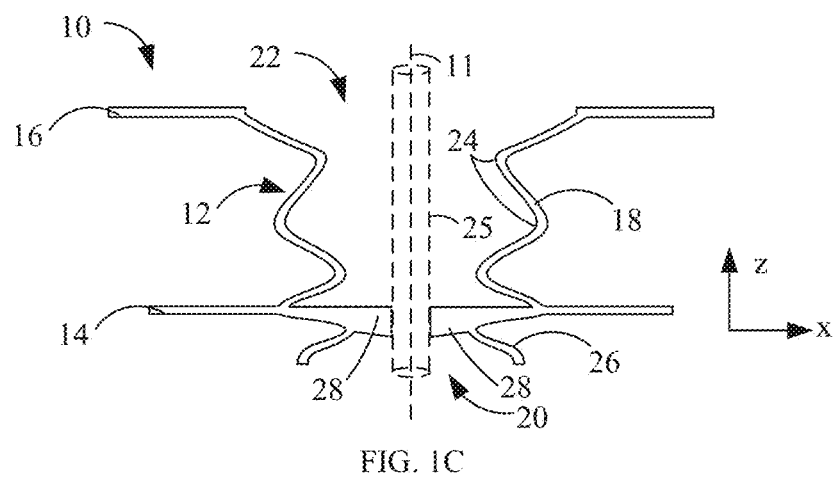
FIG. 1C is a cross sectional view of the device of FIG. 1A.
Figure 1D:
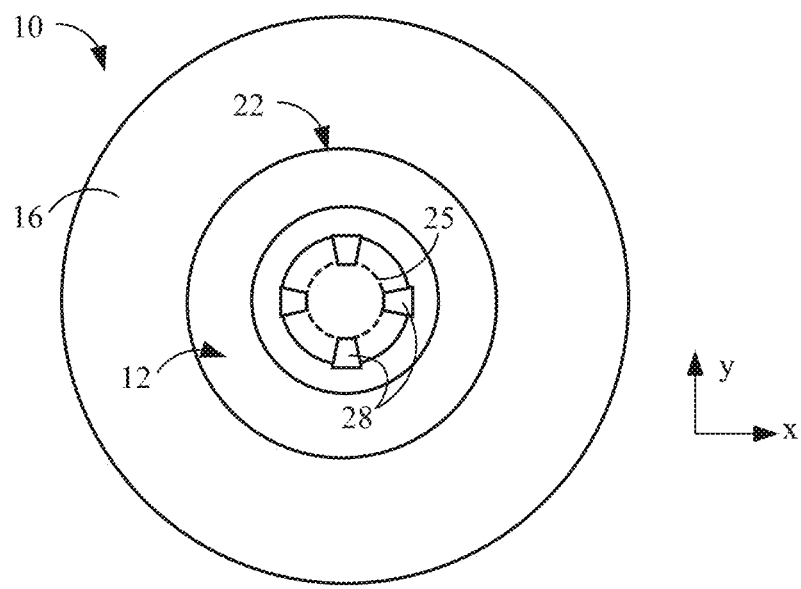
FIG. 1D is a top view of the device of FIG. 1A.
Figure 1E:
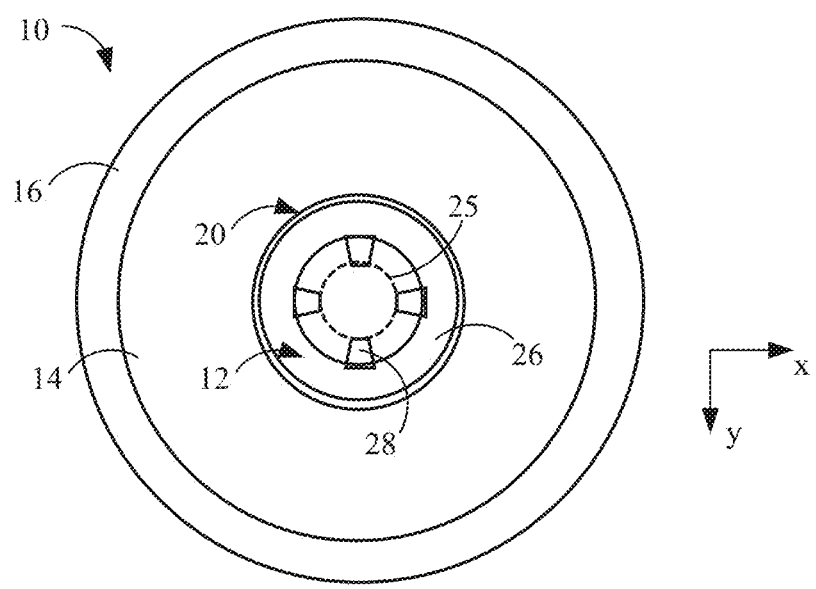
FIG. 1E is a bottom view of the device of FIG. 1A.

FIGS. 1A-1E illustrate various views of an example device 10 for managing the passage of fluid through an opening in the body of a patient. In particular, FIG. 1A is a perspective view of device 10; FIG. 1B is a side view of device 10; FIG. 1C is a cross-sectional view of device 10 taken along its longitudinal axis 11 of device 10; FIG. 1D is an upper-aerial view of device 10 looking at second flange 16; and FIG. 1E is a lower-aerial view of device 10 looking at first flange 14.

Device 10 of FIGS. 1A-1E includes a fluid-containment receptacle 12, a first flange 14, and second flange 16. Fluid-containment receptacle 12 includes a sidewall 18 that extends along longitudinal axis 11 with fluid-containment receptacle 12 having a first receptacle opening 20 and a second receptacle opening 22 positioned at opposite ends of sidewall 18 relative to longitudinal axis 11. Sidewall 18 of fluid-containment receptacle 12 defines an inner volume that allows the passage of fluid (e.g., bodily fluids) through device 10 from first receptacle opening 20 to second receptacle opening 22.

First flange 14 and second flange 16 may each be in the shape of an annular disk that extends radially from sidewall 18 (e.g., radially outward relative to longitudinal axis 11). The respective flanges may be made of flexible materials (e.g., silicone rubber) that allow the flanges to conform to non-planar surfaces such as the skin of a patient. In some examples, the annular disk shapes of first flange 14 and second flange 16 may share a common axis (longitudinal axis 11) and define parallel planes to one another. Additionally, in some examples, first flange 14 may define a smaller outer diameter than second flange 16.

First flange 14 and second flange 16 may be positioned near the opposite ends of fluid-containment receptacle 12 relative to longitudinal axis 11 such that first flange 14 is positioned at or adjacent to first receptacle opening 20 and second flange 16 is positioned at or adjacent to second receptacle opening 22. In examples, where first flange 14, second flange 16, or both are positioned at the respective receptacle opening of fluid-containment receptacle 12, the respective flange may be characterized as defining part of the receptacle opening. For example, in FIGS. 1A-1E, second flange 16 is positioned at second receptacle opening 22 such that the inner diameter of the annular shape of second flange 16 forms the second receptacle opening 22 leading into fluid-containment receptacle 12.

First flange 14 and first receptacle opening 20 may be configured to be applied to an opening in the body of the patient. Such openings may include, but are not limited to, drainage or other surgical incisions, open wounds, bodily orifices, and the like. As described further below, first receptacle opening 20 and first flange 14 may be positioned in contact with the body of the patient and form a fluid barrier against the body around the opening to seal or substantially inhibit the passage of fluids between the points of contact between device 10 and the body of the patient. As described in further detail below, second flange 16 and second receptacle opening 22 may serve as an interface for seating absorbent dressings, pouch appliances, or other devices for the purpose of capturing any fluid that passes through the inner volume defined by fluid-containment receptacle 12 and out second receptacle opening 22.

Sidewall 18 may be formed from a flexible material such that fluid-containment receptacle 12 may be collapsible along longitudinal axis 11. As used herein, "collapse," "collapsible," and variations thereof means that the structure (e.g., sidewall 18), folds, compresses, stacks, or otherwise decreases upon itself under the exertion of a compressive force. In some examples, sidewall 18 may fold upon itself to form a region that has a doubled wall; however, embodiments where two or more discrete (unconnected and independent) pieces or walls that slide, telescope, or otherwise moved in an overlapping relation to each other to reduce a collective length of the pieces is not considered to be a collapse of the pieces in context of this disclosure. In some examples, having sidewalls 18 be collapsible may allow device 10 to compress toward the incision or body orifice in the patient and ensure a positive seal around the opening.

Fluid-containment receptacle 12 may be collapsible along longitudinal axis 11 (e.g., the z-axis in FIGS. 1A-1E) from a first height (e.g., a non-collapsed or relaxed height) to a second height (e.g., collapsed height) less than the first height when subject to a compressive force applied to device 10 along longitudinal axis 11. In some examples, the first height may be at least about 1 inch (e.g., about 2.54 centimeters (cm)) such as at least about 3 inches (e.g., about 7.62 cm). The second height is less than the first height and may be equal to or less than about 1 inch (e.g., about 2.54 cm) such as equal to or less than about 0.5 inches (e.g., about 1.27 cm), or equal to or less than about 0.25 inches (e.g., about 0.63 cm). In some examples, the compressibility ratio (e.g., the second height:the first height) may be less than about 1:1 to about 1:12, however, other compressibility ratios may also be used. The rigidity and thus collapsibility of device 10 can be adjusting by modifying the material and thickness of sidewall 18, by including features such as ribs or pleats in sidewall 18, or both.

In some examples, sidewall 18 may collapse or compress along longitudinal axis 11 of fluid-containment receptacle 12, by forming folds, creases, or the like in sidewall 18. For example, as shown in FIG. 1C, sidewall 18 may include a plurality of pleats 24 configured to facilitate the collapse of device 10 when compressed along longitudinal axis 11. Pleats 24 may provide sidewall 18 with an accordion or bellows-like shape and permit sidewall 18 to bend and deflect relative to longitudinal axis 11 to accommodate the movement of the patient or medical tube 25. At least some, all, or a majority of pleats 24 may be positioned along sidewall 18 between first flange 14 and second flange 16 so that the collapse of device 10 draws first and second flanges 14 and 16 into closer relative proximity towards one another. In some examples, pleats 24 may also give fluid-containment receptacle structural strength so device 10 maintains contact with the body of the patient even when device 10 is subjected to radial forces and/or bending moments.

Apart from being collapsible, sidewall 18 may maintain the shape of device 10 when subject to radial or bending forces. For example, when used to stabilize a medical tube 25, patient movement (e.g., rolling over in bed) can press tube 25 against part of device 10 putting bending moments and radial forces on the device. The structural design of fluid-containment receptacle 12, sidewall 18, and first and second flanges 14 and 16 may enable device 10 to collapse along longitudinal axis 11 while also providing structural strength to resist buckling or folding over of device 10 in a direction transverse to longitudinal axis 11.

In some examples, fluid-containment receptacle 12 may also include one or more optional flexible skirts 26. Skirt 26 may be defined by part of sidewall 18 and may be characterized as the lower portion of fluid-containment receptacle 12 which extends longitudinally past (e.g., in the direction of longitudinal axis 11) first flange 14. When present, skirt 26 may define first receptacle opening 20 such that first flange 14 is set longitudinally back from first receptacle opening 20 (e.g., set back in the direction of the z-axis). In such examples, first flange 14 may be characterized as being adjacent to first receptacle opening 20.

Skirt 26 may help create part of the fluid barrier against the body of the patient to help establish a fluidic seal around first receptacle opening 20 at the opening in the patient. Used in conjunction with first flange 14, the two components may help form a complementing and redundant fluid barrier against the body of the patient. In examples where skirt 26 is excluded or otherwise removed from device 10, the lower surface of first flange 14 may sit flush with the body of the patient.

In some examples, fluid-containment receptacle 12 may include one or more tube retainers 28 that each extend radially inward from an inner surface of sidewall 18 towards longitudinal axis 11. The one or more tube retainers 28 are collectively configured to contact medical tube 25 when the tube is inserted through device 10 to limit axial motion of medical tube 25 through device 10. Additionally, or alternatively, tube retainers 28 may help center medical tube 25 within fluid-containment receptacle 12 along longitudinal axis 11 and prevent radial movement (e.g., relative to longitudinal axis 11) of medical tube 25 relative to device 10. As described further below, depending on the design and shape of tube retainers 28, the one or more retainers may form a fluid barrier against the external surface of medical tube 25 to inhibit fluid leakage between tube retainers 28 and medical tube 25. In other examples, tube retainers 28 may form a non-fluidic seal with medical tube 25 to permit the passage of leaked fluid through the inner volume of device 10 so that the leaked fluid can be collected at second receptacle opening 22.

In some examples, one or more of first flange 14, second flange 16, and skirt 26, tube retainers 28, or other portions of device 10 may be configurable by the user (e.g., can be cut to fit using a pair of scissors) so that device 10 may be trimmed to the specific size or shape requirements needed for a specific application. For example, first flange 14 and skirt 26 (if present) may be custom cut for each patient (e.g., at bedside) to adapt device 10 to seal to irregularities in the patients skin or to help hold device 10 in position relative to the patient when device 10 is placed subcutaneously to help ensure fluid leakage is managed. In some examples, first flange 14 and skirt 26 may be configurable by changing the relative diameter of the respective components. Additionally, or alternatively, tube retainers 28 may be configurable (e.g., can be cut to fit) to accommodate different diameter medical tubes 25.

Any suitable material may be used to form all or part of device 10. In some examples, device 10 may be formed from one or more biocompatible, sterilizable, materials including, for example, plastics or rubbers, as will be recognized by those skilled in the art. In some examples, device 10 may include a silicone rubber. Other materials may be used, for example, a flexible thermoplastic. Preferably, device 10 is formed using a non-fluid permeable and/or non-porous flexible material. Further, as will be recognized by those skilled in the art, the devices can be sized and shaped to accommodate all different sizes and shapes of incisions, body orifices, and medical tubes.

In some examples, device 10 may be sterilized for use in a surgical environment. Additionally, or alternatively device 10 or kit for a fluid management system that includes device 10 may be sterilized and packaged in a seal pouch or container that preserves the sterility of device 10 and can be opened by the patient or clinician.

The devices described herein, including device 10, may include any or all of the following optional features shown and described with respect to the additional examples of FIGS. 2A to 6D. The features disclosed and described in the context of FIGS. 2A to 6D may be used in combination with any of the other features described herein such that it will be understood that any feature or specific combination of features shown in the accompanying figures is not intended to be limited to only the specific embodiments illustrated.

Figure 2A:
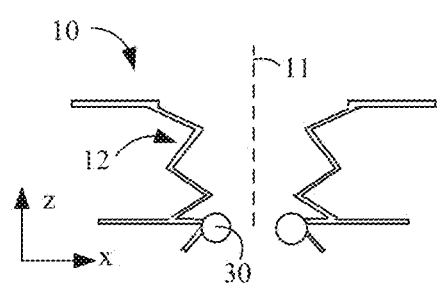
Figure 2B:
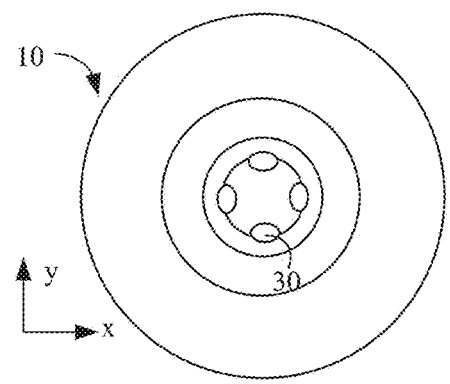
Figure 2C:
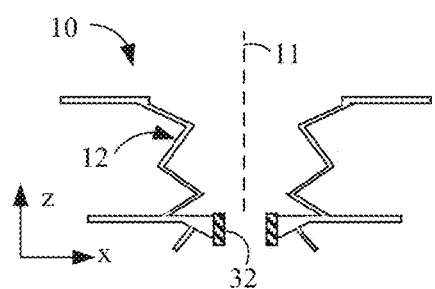
Figure 2D:
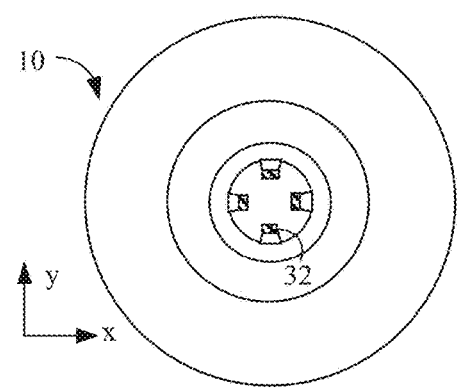
Figure 2E:
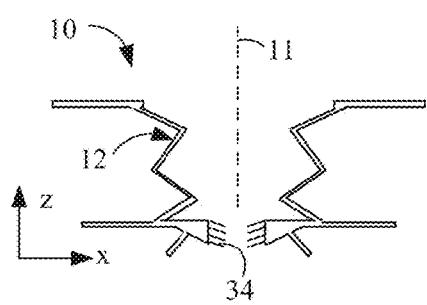
Figure 2F:
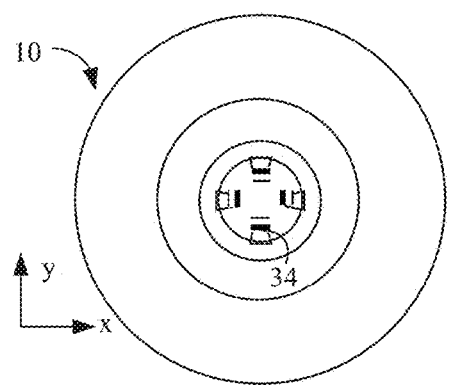

FIGS. 2A-2L illustrate various cross-sectional (FIGS. 2A, 2C, 2E, 2G, 2I, and 2K) and aerial (FIGS. 2B, 2D, 2F, 2H, 2J, and 2L) views of optional placements and constructions for tube retainers 28, which may be used with device 10 of FIGS. 1A-1E. FIGS. 2A and 2B show device 10 with tube retainers 28 in the form of retention bulbs 30 positioned inside fluid-containment receptacle 12 in-plane with first flange 14. Bulbs 30 may be composed of a solid or hollowed material configured to contact and help center and restrain medical tube 25. FIGS. 2C and 2D show device 10 with adhesive, sealant, or hydrocolloid 32 deposited on at least a portion of tube retainers 28 such that adhesive, sealant, or hydrocolloid 32 will interact with medical tube 25 to help restrain axial movement of the tube. FIGS. 2E and 2F show device 10 with retention hooks 34 on the contacting surfaces of tube retainers 28. Hooks 34 are positioned inside of fluid-containment receptacle 12 and configured to interact with medical tube 25. In some examples, depending of the directionality of hooks 34, the retainers may help prevent movement of medical tube 25 in at least one axial direction.

Figure 2G:
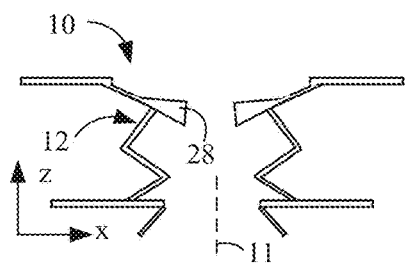
Figure 2H:
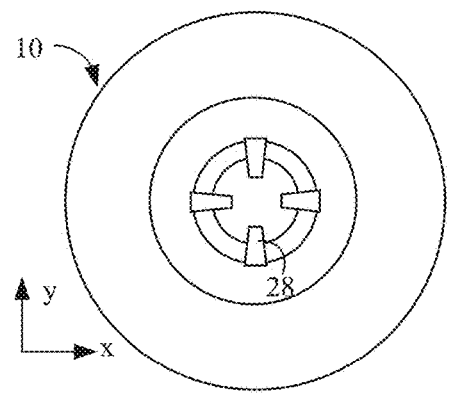
Figure 2I:
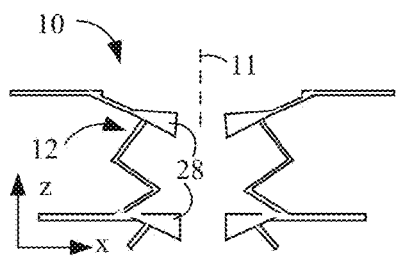
Figure 2J:
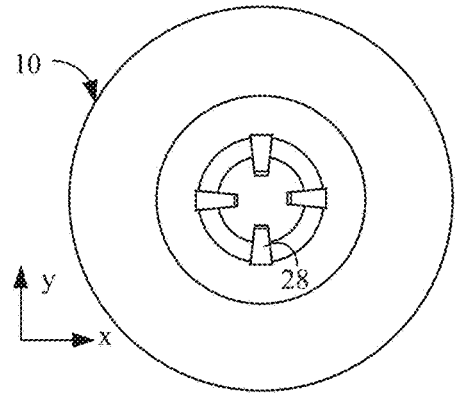
Figure 2K:
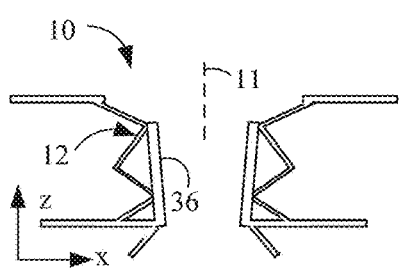
Figure 2L:
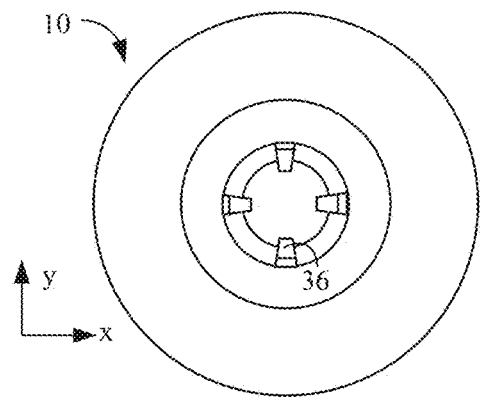

In some examples, other devices can be used in place of hooks 34 to accomplish a similar function. Such alternative devices may include, but are not limited to, ridges, burs, fins, or the like. FIGS. 2G and 2H show device 10 with tube retainers 28 positioned inside fluid-containment receptacle 12 in a position adjacent to second receptacle opening 22 such that tube retainers 28 are positioned in closer proximity to second opening 22 than first opening 20. The configuration of FIGS. 2G and 2H may help center medical tube 25 closer to second flange 16 which may be useful in examples where device 10 is mounted subcutaneously. FIGS. 2I and 2J show device 10 with two sets of tube retainers 28 position adjacent to both first receptacle opening 20 and second receptacle opening 22 (e.g., in-plane with first and second flanges 14 and 16 respectively). The configuration of FIGS. 2I and 2J may help center medical tube 25 near both first and second flanges 14 and 16 for additional support and isolation. FIGS. 2H and 2I show device 10 with tube retainers 28 in the form of tube retention strips 36 running the length of fluid-containment receptacle 12 between first opening 20 and second opening 22. Tube retention strips 36 may be connected to sidewall 18 at one or more of pleats 26 and may establish a partial double wall.

In some examples, device 10 may also include an optional retention sleeve configured to help secure device 10 to medical tube 25. FIGS. 3A-3H illustrate various cross-sectional (FIGS. 3A, 3C, 3E, and 3G) and aerial (FIGS. 3B, 3D, 3F, and 3H) views of another example device 40, which includes fluid-containment receptacle 12, sidewall 18, first flange 14, and second flange 16 substantially as described above with respect to device 10 apart from any differences noted below. Device 40 further includes the presence of a retention sleeve 42 which may be used in addition or as an alternative to tube retainers 28. Like tube retainers 28, retention sleeve 42 is configured to contact a medical tube 25 (not shown in FIGS. 3A-3H) when the tube is inserted through device 40 to limit axial and radial motion of medical tube 25 through device 40. Retention sleeve 42 may be positioned at any suitable point along sidewall 18 of device 40 and may be considered as forming part of sidewall 18. In some examples, retention sleeve 42 may form the end of fluid-containment receptacle 12 that is not intended to be positioned in contact with the body of the patient (e.g., the end opposite to first receptacle opening 20). In some such examples, retention sleeve 42 may define at least a portion of second receptacle opening 22. Second flange 16 may be positioned along retention sleeve 42 or positioned in closer relative proximity thereto.

As shown in FIGS. 3A-3H, second flange 16 may be positioned at one of pleats 26 along sidewall 18 such that sidewall 18 includes a tapered section 43 that tapers radially inward from second flange 16 before forming retention sleeve 42. In some examples, tapered section 43 may include one or more optional apertures that allow the passage of leaked fluid through fluid-containment receptacle 12 so that the fluid can be collected near second flange 16. In other examples, tapered section 43 may be impervious to fluid. In all such examples, second flange 16 may be considered as being positioned adjacent to second receptacle opening 22.

Figure 3A:
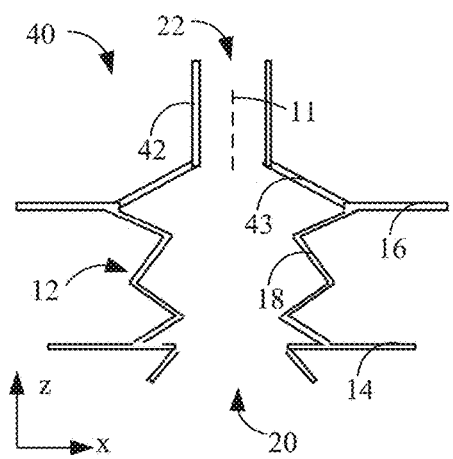
Figure 3B:
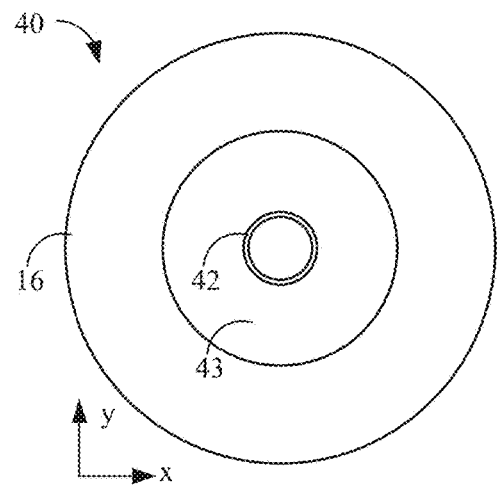
Figure 3C:
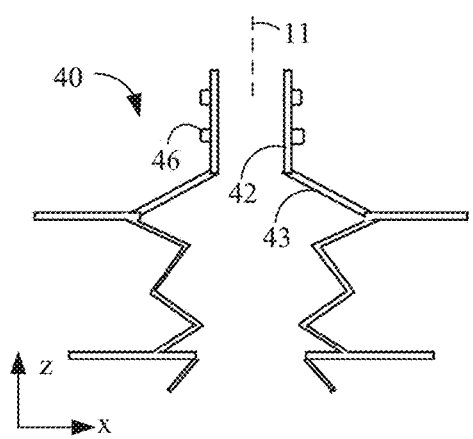
Figure 3D:
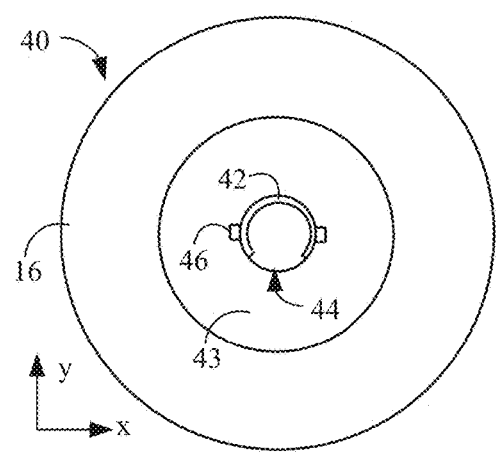

FIGS. 3A and 3B show device 40 with a tube retention sleeve 42 extending along the end of sidewall 18 with tube retention sleeve defining at least a portion of second receptacle opening 22. In this example, retention sleeve 42 may be tubular in shape and may form a complete cylindrical ring about longitudinal axis 11. FIGS. 3C and 3D show device 40 with tubular retention sleeve 42 further defining a longitudinal slot 44 (best seen in FIG. 3D) that extends parallel to longitudinal axis 11 such that retention sleeve 42 does not form a complete loop around longitudinal axis 11. Slot 44 may allow retention sleeve 42 the ability to change in relative internal diameter when being secured to medical tube 25 to accommodate different diameter medical tubes. Additionally, or alternatively, retention sleeve 42 may include one or more retainers 46 positioned along the exterior surface of retention sleeve 42. Retainers 46 may take on the form of a raised ridge, ring, or other suitable physical structure that can aid in fastening device 40 to medical tube 25 via tape, zip-tie, or the like by preventing axial motion of the tape, zip-tie, or other fastener relative to retention sleeve 42.

Figure 3E:
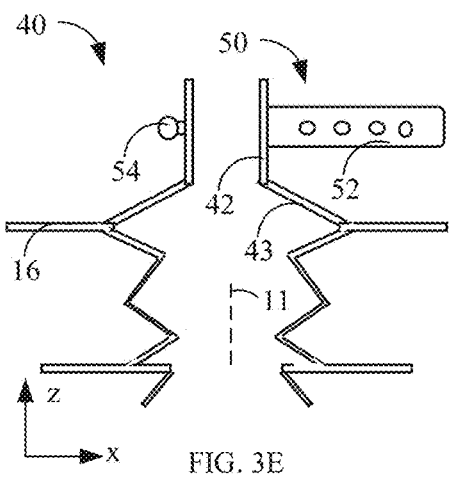
Figure 3F:
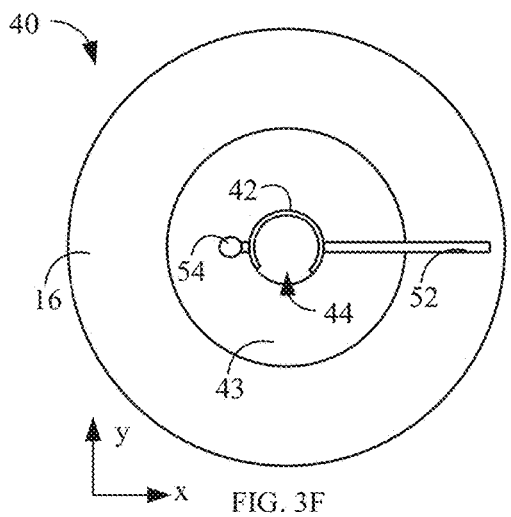
Figure 3G:
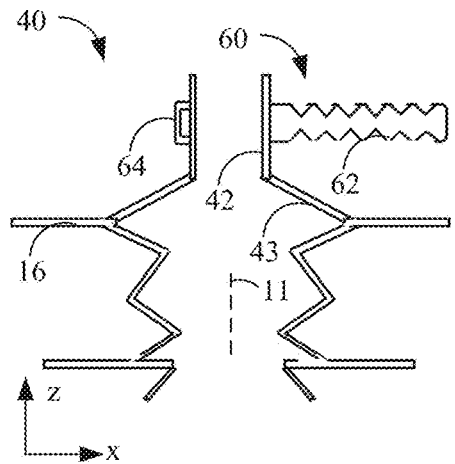
Figure 3H:
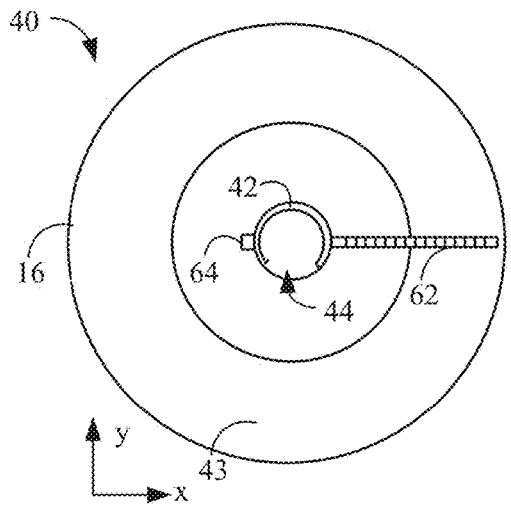

FIGS. 3E and 3F show device 40 with retention sleeve 42 including slot 44 and further including an integral fastener 50 that includes a fastening strap 52 defining a plurality of apertures and a fastening button or hook 52 configured to be received by the plurality of apertures in strap 52 when the strap is wrapped around retention sleeve 42 and medical tube 25 to secure retention sleeve 42 to medical tube 25. FIGS. 3G and 3H show device 40 with retention sleeve 42 and another example integral fastener 60 that includes an elongated strap 62 defining a sawtooth-type pattern along at least part of the perimeter of strap 62 and a strap retainer 64 configured to mechanically receive strap 62 to secure retention sleeve 42 to medical tube 25. Both fasteners 50 and 60 may be integrally formed on the exterior surface of retention sleeve 42. Other mechanical type fasteners may also be used with retention sleeve 42

In some examples, device 10 may exclude the presence of tube retainers 28 and/or retention sleeve 42. FIGS. 4A-4D illustrate various cross-sectional (FIGS. 4A and 4C) and aerial (FIGS. 4B and 4D) views of example configurations for fluid-containment receptacle 12 of device 10 of FIGS. 1A-1E that exclude the presence of tube retainers 28 or retention sleeve 42. As discussed further below with respect to FIGS. 10A and 10B, excluding the presence of tube retainers 28 or retention sleeve 42 may be useful for drainage incisions where device 10 is not used in conjunction with medical tube 25 or where retention of medical tube 25 by device 10 is not prioritized.

Figure 4A:
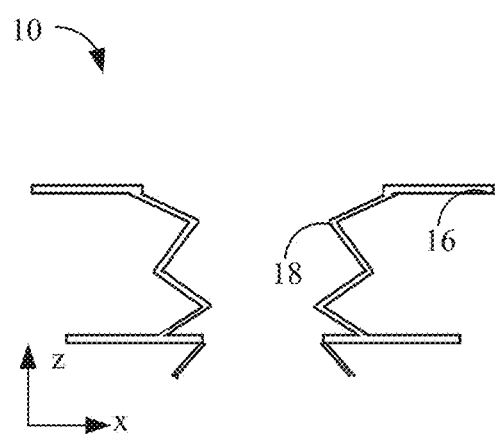
Figure 4B:
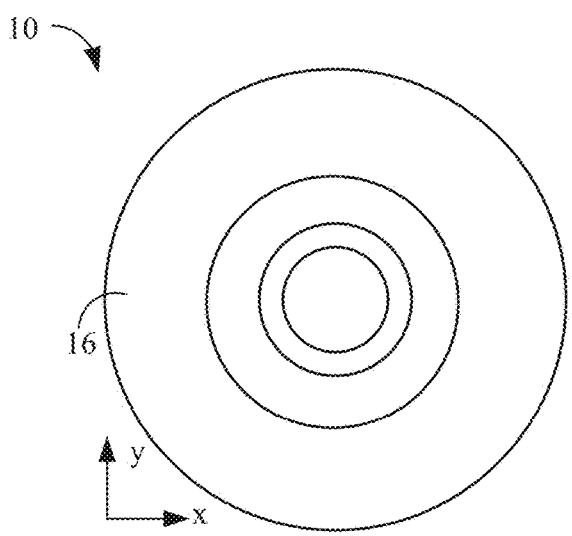
Figure 4C:
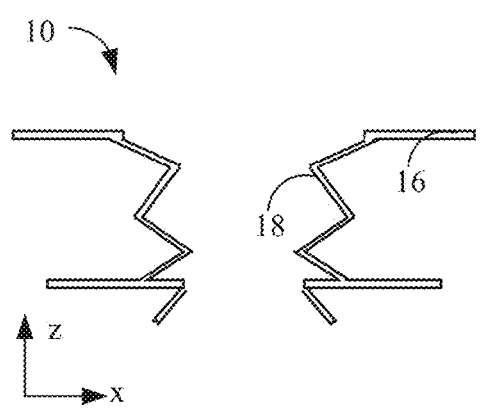
Figure 4D:
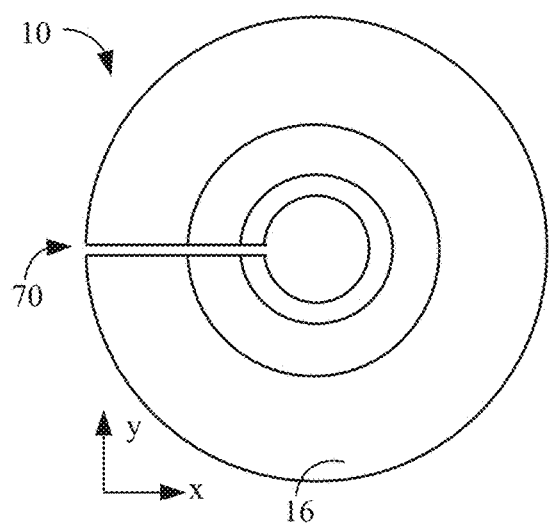

Device 10 of FIGS. 4C and 4D also includes the presence of a slit 70 defined by device 10 that extends longitudinally along sidewall 18 completely through device 10. Having slit 70 may allow for device 10 to be installed over medical tube 25 or other apparatus at a midway point along the tube or apparatus. Additionally, or alternatively, slit 70 may help to temporarily reduce the outer diameter of fluid-containment receptacle 12 so that it may be more easily inserted into an incision.

Figure 5A:
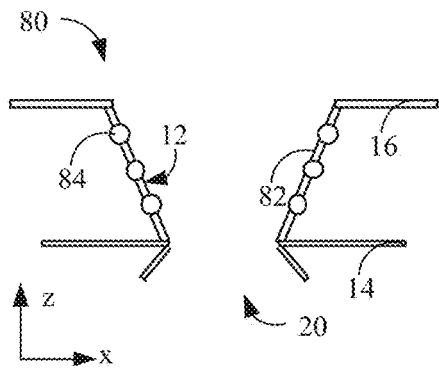
Figure 5B:
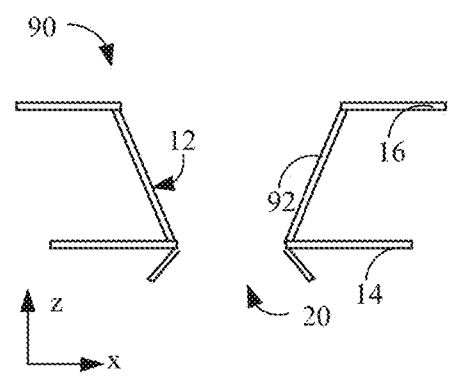

FIGS. 5A and 5B are cross-sectional views of example devices 80 and 90 respectively showing additional example constructions for fluid-containment receptacle 12. Devices 80 and 90 include a fluid-containment receptacle1 2 having sidewalls 82 and 92 respectively, both of which define a taper of reducing diameter from second flange 16 to first flange 14 such that the inner diameter of sidewalls 82 and 92 at first flange 14 is less than the inner diameter at second flange 16. Device 80 of FIG. 5A is shown with a plurality of ribs 84 formed along sidewall 82. Ribs 84 may permit fluid-containment receptacle 12 to collapse along longitudinal axis 11 while still providing sufficient structural support in the radial direction to device 80. Ribs 84 may also minimize the outside diameter of device 80 in its collapsed state to minimize pressure against the incision opening and wound aggravation in a subcutaneous application. Device 90 of FIG. 5B is shown with sidewall 92 including flat or smoothly curved inner surface. A flat or smoothly curved sidewall 92 may be desirable in gastric feeding tube applications to minimize the collapse of device 90 and maximize the stand-off height of the tube from the patient's skin.

Figure 6A:
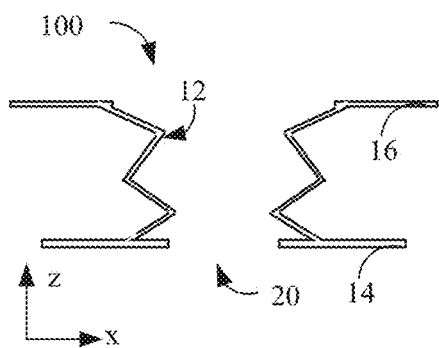

FIGS. 6A-6D are cross-sectional views of example devices that show example configurations for shaping skirt 26 and/or first receptacle opening 20 that may be used with the device 10 of FIGS. 1A-1E to help establish a fluid barrier between the device and the body of a patient. More specifically, FIG. 6A shows an example device 100 that excludes the presence of skirt 26. By excluding the presence of skirt 26, first flange 14 is positioned at first opening 20 such that first flange 14 defines at least part of first opening 20. Skirt 26 may be excluded from the making of device 100 or may be removed (e.g., cut) from the device by the user. The configuration of device 100 may allow for first flange 14 to sit flush with the body of the patient when installed.

Figure 6B:
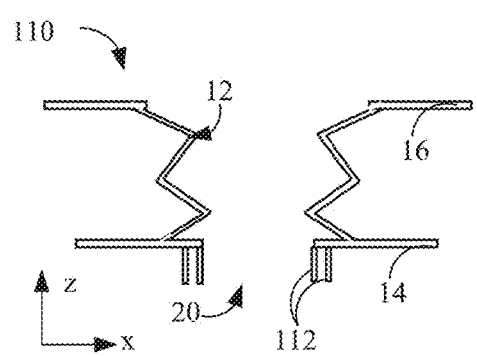

FIG. 6B shows an example device 110 having a plurality of flexible skirts 112 each extending longitudinally from a lower surface (e.g., the surface configured to be brought in contact with the patient) of first flange 14. Skirts 112 may help form a redundant seal at the opening in the body of the patient between the body and first receptacle opening 20. Skirts 112 may extend from part of fluid-containment receptacle 12, first flange 14, or both.

Figure 6C:
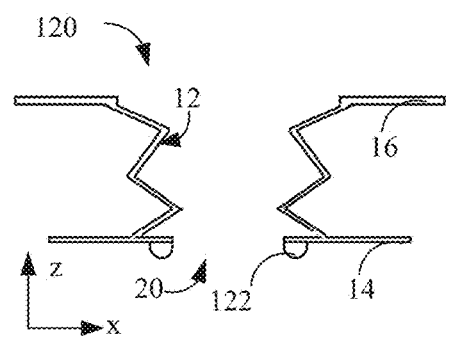

FIG. 6C shows an example device 120 which includes a bulb seal 122 formed around the perimeter of first receptacle opening 20. In some examples, bulb seal 122 may take the form of a raised ring that extends longitudinally from a lower surface (e.g., the surface configured to be brought in contact with the patient) of first flange 14 and encircles first receptacle opening 20 to help form the fluid barrier at the opening in the body of the patient.

Figure 6D:
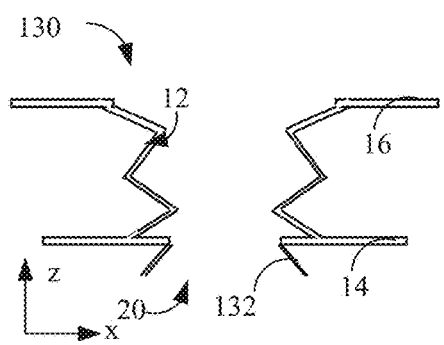

FIG. 6D shows and example device 130 that includes a tapered skirt 132 that flares radially and longitudinally outward from the lower surface of first flange 14. Skirt 132 may be at least partially collapsed when applied to the body of a patient to help form the fluid barrier between skirt 132 and the body of the patient.

FIGS. 7A to 10B show the devices described herein being used in conjunction with various fluid management systems. For ease of illustration, the systems are primarily described as including device 10 of FIGS. 1A-1E, however other devices and/or device features as described herein also may be incorporated into the devices shown in FIGS. 7A to 10B or used with other fluid management systems.

Figure 7A:
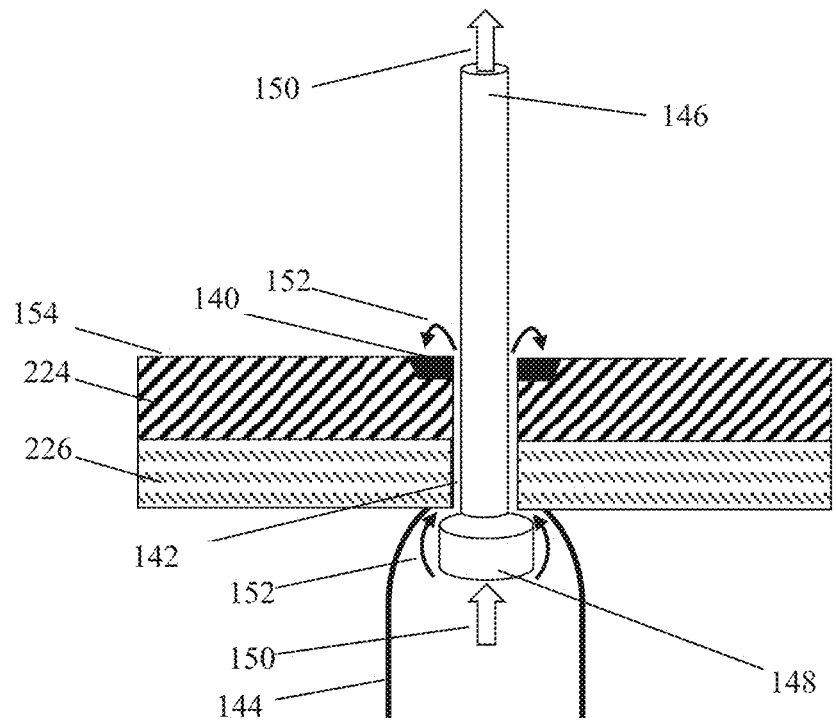
FIG. 7A is a cross-sectional view of an example fecal management system inserted in a rectum and showing stool leakage around the fecal management system onto the perineum of a patient.
Figure 7B:
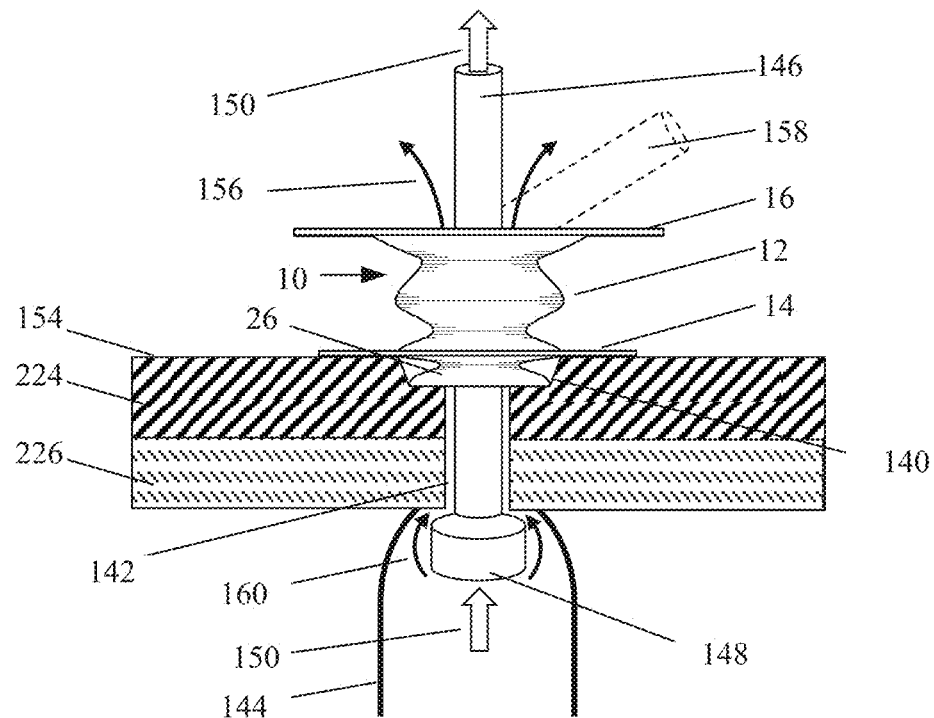
FIG. 7B is a side view of the example device of FIG. 1A, installed on the fecal management system of FIG. 7A.

FIGS. 7A and 7B show device 10 being used in conjunction with a fecal management system. FIG. 7A shows a cross-sectional view of an anus 140, rectum 142, and colon 144 in which a fecal management system has been placed. The relevant portions of the fecal management system include the fecal management tube 146 with an attached balloon or stent seal 148 which is intended to be placed against the rectum 142 so that fecal matter 150 is directed into the fecal management tube 146 and outside the body.

Fecal management systems are designed to create a seal against the internal rectal cavity with a balloon or stent seal 148. However, the seal between balloon or stent 148 and the rectum 142 may be imperfect due to, for example, poor seals and weak sphincter tone. The weak seal can lead to fecal matter leakage (illustrated by arrows 152) around the perimeter of the fecal management tube 146 at the anus 140 and onto the skin 154 of the patient (e.g., the perineal). Conventional fecal management systems claim leakage rates on the order of 5-20% as disclosed by the manufactures. This uncontrolled leakage of stool (arrows 152) may be problematic for patients with open wounds near the anus such as Fournier's gangrene, necrotizing fasciitis, and perineal burns that need to heal and/or be skin grafted.

In some examples, a common practice for managing fecal matter leakage in these cases is the creation of a diverting loop ileostomy. An estimated 100,000 diverting loop ileostomies are created in the United States each year, requiring an initial bowel surgery to divert fecal matter into a pouching system followed by a second surgery to reconnect the bowel after the patient condition has improved. This is a costly solution that diminishes the quality of life for the patient and carries with it an estimated mortality risk of about 0.1-4% and potential for complications such as wound infection and small bowel obstruction which increase medical costs, prolong hospitalization time, and increase the need for outpatient care. The devices of the present disclosure may help reduce or inhibit stool leakage associated with such fecal management systems and reduce the need to establish a diverting loop ileostomy.

FIG. 7B shows the employment of an example device as described herein (e.g., device 10 of FIGS. 1A-1E) used to help isolate and/or stabilize fecal management tube 146 and reduce or prevent stool leakage (arrows 152) from occurring. As shown in FIG. 7B fecal management tube 146 is put through the inside of device 10 with first flange 14 of device 10 placed against skin 154 surrounding anus 140. Optional flexible skirt 26 at first receptacle opening 20 forms a fluid barrier around anus 140 and first flange 14 forms a complementary fluid barrier against perineal skin 154. Fecal management tube 146 conducts primary fecal matter drainage from the colon 144 through the rectum 142 to a fecal management collection appliance (not illustrated). In some examples, device 10 may form a fluid seal against the skin 154 around anus 152 such that any stool leakage between the anal sphincter and fecal management tube 146 is contained and redirected away from skin 154. The redirected leakage (shown by arrows 156) may be captured by an absorbent dressing, pouch appliance, or other article attached to second flange 16 around second receptacle opening 22. Thus, device 10 may help prevent or substantially reduce the likelihood of fecal matter from coming into contact with skin 154 surrounding anus 140 which can help enable healing and/or skin grafting of patients with, for example, Fournier's gangrene, necrotizing fasciitis, burns, or other perineal wounds.

Additionally, or alternatively, device 10 may provide radial support for fecal management tube 146 when the tube is bent 158 to reduce the likelihood of the tube crimping or plugging. Tube retainers 28 on device 10 may also help support fecal management tube 146 axially to hold the fecal management tube balloon or stent seal 148 against rectum 142 and reduce leakage around the fecal management tube 146 (shown by arrows 160 in FIG. 7B).

Figure 8A:
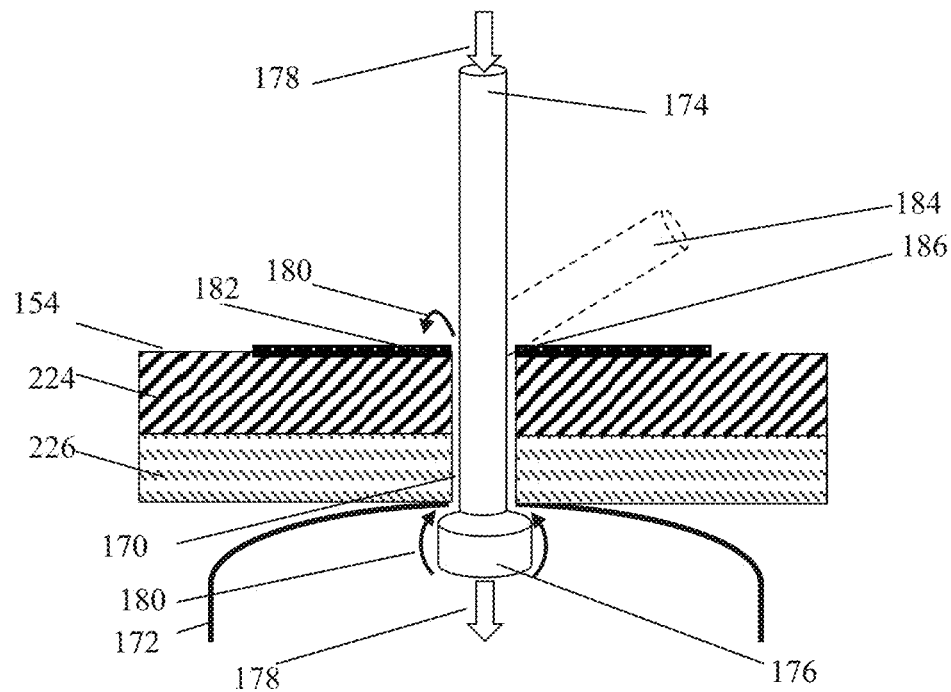
FIG. 8A is a cross-sectional view of an example gastric tube inserted through an abdominal wall and showing fluid leakage around the gastric tube onto the skin of a patient.

FIG. 8A shows a cross-sectional view of an incision 170 and stomach 172 in which a gastric feeding system has been placed. The relevant portions of the gastric feeding system include a gastric feeding tube 174 with an attached balloon seal 176 which is intended to be placed against the inside wall of stomach 172 to form a seal that keeps gastric juices in stomach 172 while nutritional formula 178 is put through the gastric feeding tube 174 and into the patients stomach 172. However, the seal between the gastric feeding tube balloon seal 176 and stomach 172 may be imperfect and gastric juice can leak (shown by arrows 180) around the perimeter of gastric feeding tube 174 through incision 170 and onto skin 154 surrounding the tube incision 170. This unintended gastric juice leakage may create a surface wound 182 by irritating and breaking down skin 154. Surface wound 182 may become aggravated when patient positioning and other tube management systems put gastric feeding tube 174 in a bent position 184 creating a pressure point 186 against the skin incision opening. Patient movement may also rub pressure point 186 at the edge of the incision 170 further eroding skin 154 and making the wound 182 challenging to heal. An estimated 350,000 gastric feeding tubes are placed in the United States each year, with an estimated 15-58% rate of complications such as wound infections, dislodgement, and peritonitis affiliated with such placements. The devices of the present disclosure may help reduce leakage associated with such gastric feeding tubes and reduce the likelihood of unwanted complications.

Figure 8B:
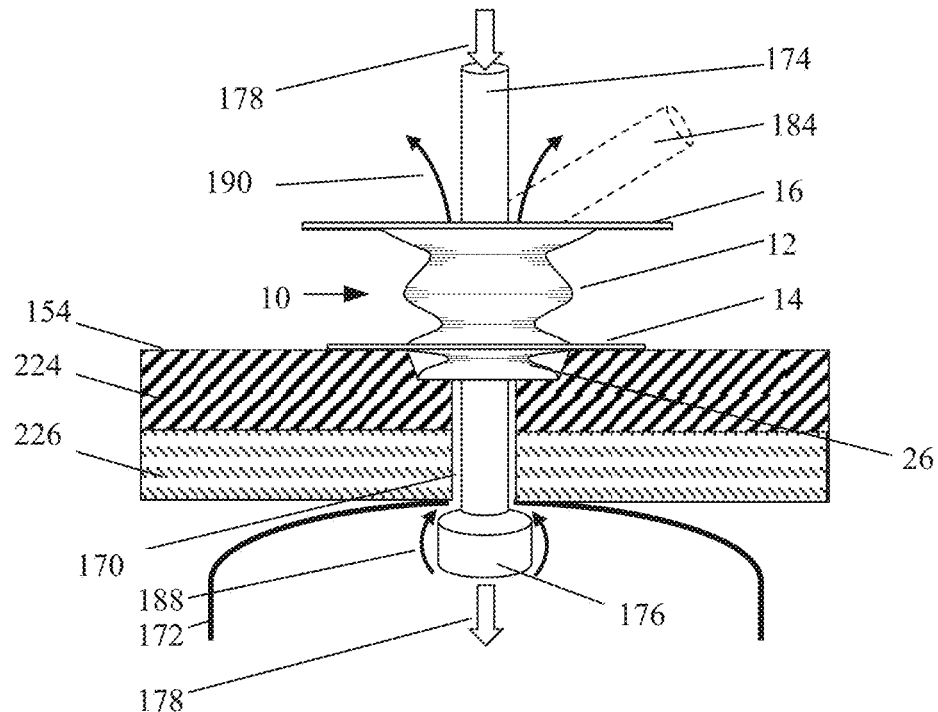
FIG. 8B is a side view of the example device of FIG. 1A, installed on the gastric tube of FIG. 8A.

FIG. 8B shows the employment of an example device as described herein (e.g., device 10 of FIGS. 1A-1E) being used to help isolate and/or stabilize tube 174 and reduce or prevent leaked gastric fluid 180 from occurring. Gastric feeding tube 174 may be put through the inside of device 10 with the lower surface of first flange 14 of device 10 being placed against skin 154 surrounding feeding tube incision 170. Flexible skirt 26 at first receptacle opening 20 may form a fluid barrier around incision 170 and first flange 14 may form a complementary fluid barrier against skin 154. Gastric feeding tube 174 conducts nutritional formula 178 through gastric feeding tube 174 and into stomach 172.

In some examples, device 10 may form a fluid barrier against the skin 154 such that any gastric juice leakage (e.g., shown by arrows 188) between incision 170 and gastric feeding tube 174 is contained and redirected. The redirected leaked fluid 190 may be captured by an absorbent dressing, pouch appliance, or other article attached to second flange 16 around second receptacle opening 22. Thus, device 10 may help prevent or substantially reduce the likelihood of leaked gastric fluid 180 from coming into contact with the skin 154 surrounding the incision 170 which may help prevent skin irritation or wound formation at the incision site to help enable healing of surface wounds adjacent to the incision 170.

Additionally, or alternatively, device 10 may provide radial support for tube 174 when the tube is bent 184, to eliminate pressure point 186 at the edge of incision 170 and prevent incision erosion and wound formation. Tube retainers 28 on device 10 may also help support gastric feeding tube 174 axially to hold the gastric feeding tube balloon seal 176 against the inside wall of stomach 172 to reduce leakage 188 around the gastric feeding tube 174.

Figure 9A:
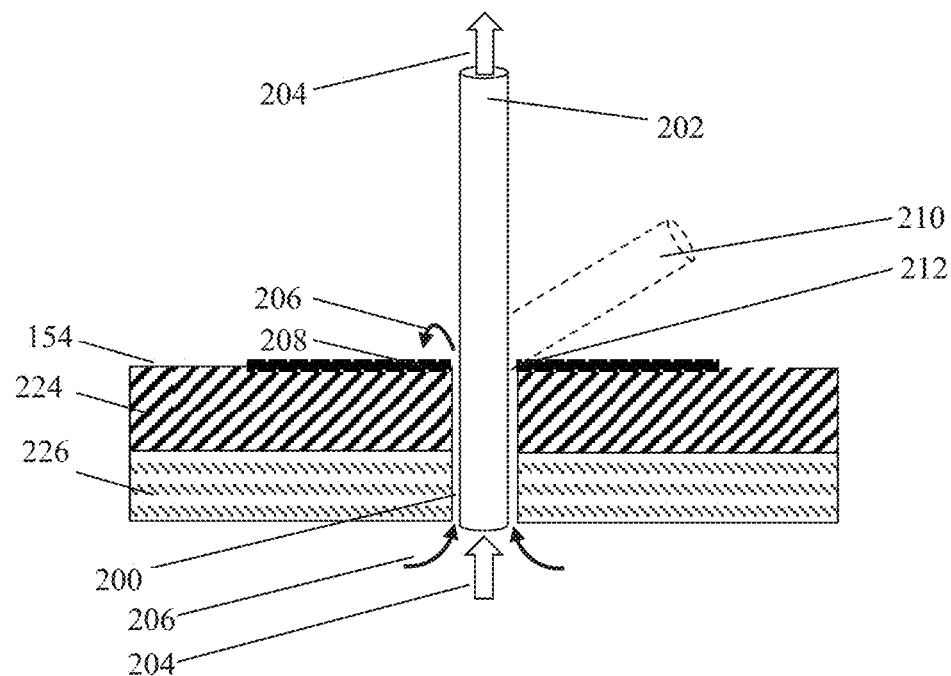
FIG. 9A is a cross-sectional view of an example wound drainage tube inserted into the body of a patient and showing fluid leakage around the wound drainage tube onto the skin of the patient.

FIG. 9A shows a cross-sectional view of an incision 200 in which a wound drainage tube 202 has been placed to conduct wound drainage 204 (e.g., wound exudate) outside the body of the patient. The opening of incision 200 may need to be supported to stay open and allow proper healing to proceed sequentially from the base of the wound to the skin. Drainage of wound exudate must not back-up inside the body or the healing process may be compromised. While tube 202 helps facilitate drainage of fluid 204, bodily fluids may also leak (shown by arrows 206) around the perimeter of the wound drainage tube 202 through the incision 200 and onto the skin 154 surrounding tube incision 200. This unintended bodily fluid leakage 206 can cause a surface wound 208 by irritating and breaking down skin 154. Surface wound 208 may become aggravated when patient positioning and other tube management systems put the wound drainage tube 202 in a bent position 210 creating a pressure point 212 against the skin incision opening. Patient movement can also constantly rub pressure point 212 at the edge of incision 200 further eroding skin 154 and making wound 208 challenging to heal.

Figure 9B:
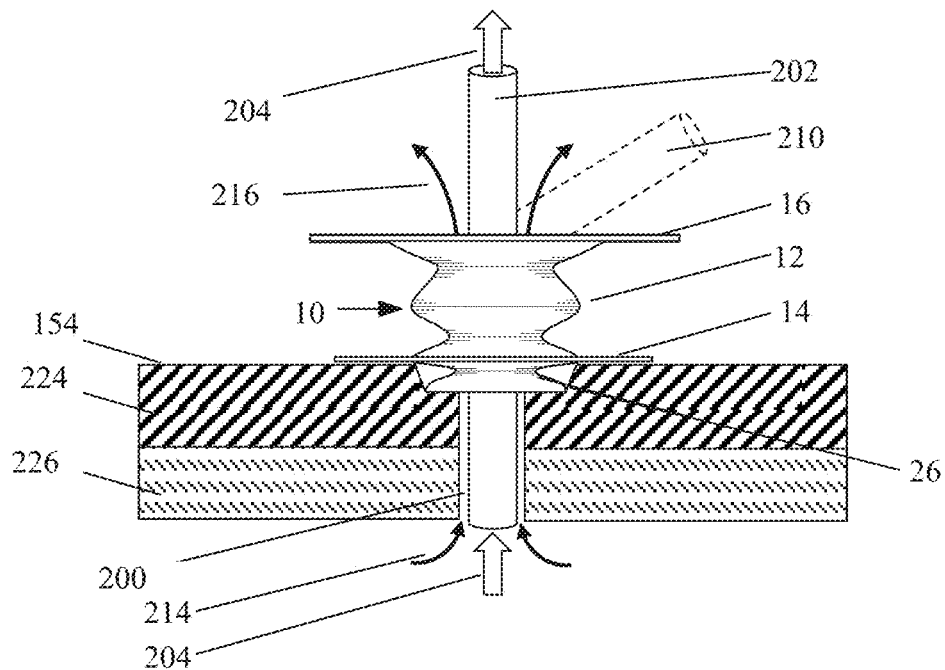
FIG. 9B is a side view of the example device of FIG. 1A, installed on the wound drainage tube of FIG. 9A.

FIG. 9B shows the employment of an example device as described herein (e.g., device 10 of FIGS. 1A-1E) being used to help isolate and/or stabilize tube 202 and reduce or prevent fluid leakage (arrows 206) from occurring. Wound drainage tube 202 may be placed through the inside of device 10 with the lower surface of first flange 14 placed against skin 154 surrounding tube incision 200. Flexible skirt 26 at first receptacle opening 20 may form a fluid barrier around incision 200 and first flange 14 may form a complementary fluid barrier against skin 154. Wound drainage tube 202 conducts wound drainage 204 from inside the body to a drainage collection appliance (not illustrated).

In some examples, device 10 may form a fluid barrier against the skin 154 such that any bodily fluid leakage (e.g., shown by arrows 214) between the incision 200 and the wound drainage tube 202 is contained and redirected. The redirected leakage 216 may be captured by an absorbent dressing, pouch appliance, or other article attached to second flange 16 around second receptacle opening 22. Thus, device 10 may help prevent or substantially reduce the likelihood of bodily fluid leakage 206 from coming into contact with skin 154 surrounding incision 200 which may help prevent skin irritation and wound formation and enable healing of surface wounds adjacent to incision 200.

Additionally, or alternatively, device 10 may provide radial support for tube 202 when the tube is bent 210, to eliminate pressure point 212 at the edge of incision 200 and prevent incision erosion and wound formation. Device 10 may also support tube 202 axially to hold the tube in position relative to incision 200.

Figure 10A:
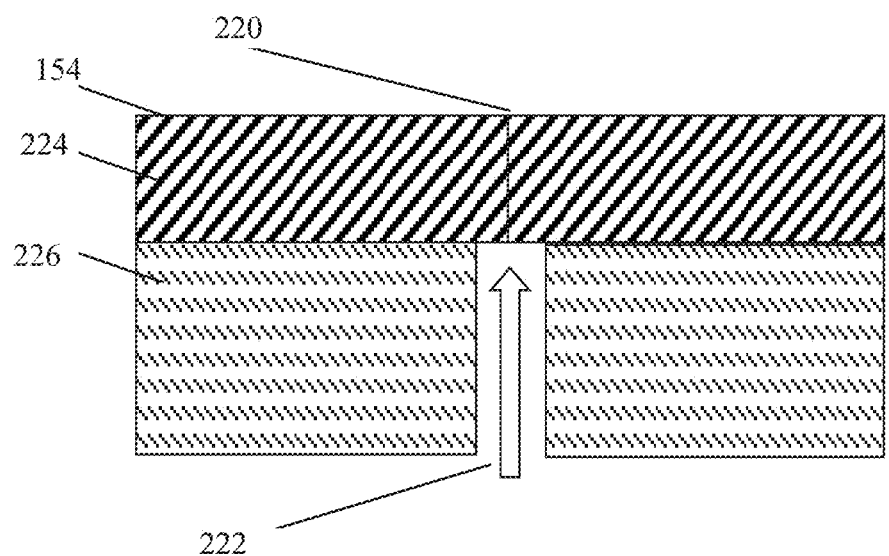
FIG. 10A is a cross-sectional view of an example wound drainage incision made in the body of a patient.

FIG. 10A shows a cross-sectional view of partially closed drainage incision 220 that does not allow wound drainage 222 to exit to outside the body of a patient. Skin 154, soft tissue layers 224, and muscle layer 226 may move together to close incision 220 prematurely.

Figure 10B:
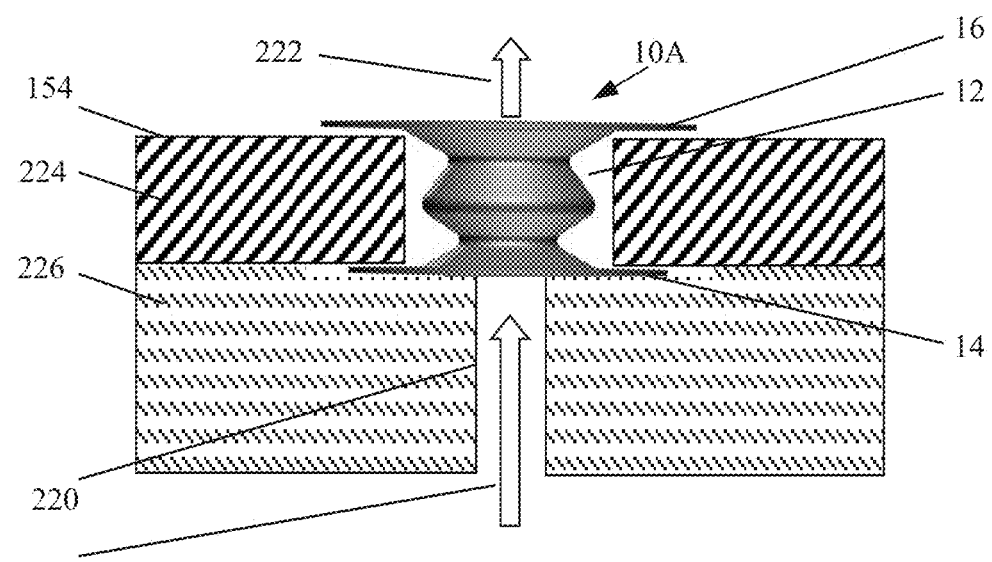
FIG. 10B is a side view of an example device, installed subcutaneously in the drainage incision of FIG. 10A.

FIG. 10B shows the employment of an example device as described herein (e.g., device 10 of FIGS. 1A-1E with skirt 26 being removed (herein referred to as device 10A)) being used to help prevent incision 220 from closing prematurely as well as redirect any wound fluid 222 away from skin 154 of the patient. As shown in FIG. 11B, device 10A may be placed subcutaneously to open drainage incision 220. With skirt 26 removed, first flange 14 may be inserted between the soft tissue 224 and muscle layers 226 to help hold device 10A in position axially relative to incision 220. In this position, device 10A may conduct wound drainage of fluid 222 from inside the body to an absorbent dressing, pouch appliance, or other article positioned at second flange 16 around second receptacle opening 22. Thus, device 10A allows the incision 220 to drain and prevents wound fluid 222 from coming into contact with the skin 154 surrounding the incision 220 which may help keep incision 220 open, prevent skin irritation, and promote healing of surface wounds adjacent to the incision 220. In some examples, tube retainers 28 may be excluded or removed from device 10A to further open up the inner volume defined by sidewall 18 to allow the passage of fluid 222 through device 10A.

While FIG. 10B shows device 10A inserted subcutaneously and used alone to manage fluid 222, in other examples, device 10A may be inserted subcutaneously and used in conjunction with medical tube 25 (e.g., tube 202 of FIGS. 9A and 9B). When used with a medical tube in the subcutaneous position of FIG. 10B, device 10A may provide one or more of the benefits discussed above including, for example, providing radial and axial support to the medical tube as well as establish a fluid barrier between device 10A and the patient to help redirect any leaked fluid that may occur between the medical tube and the device.

As described above, the devices described herein may be used in conduction one or more external wound care devices including, but not limited to, absorbent dressing, pouch appliance, or other article attached. FIGS. 11A to 12C show the employment of an example device as described herein (e.g., device 10A) used with one or more optional wound care devices such as a wound drape or belt. Any of the various options shown in FIGS. 11A to 12C may be used in any combination with any of the devices, device features, and fluid management systems described herein.

Figure 11A:
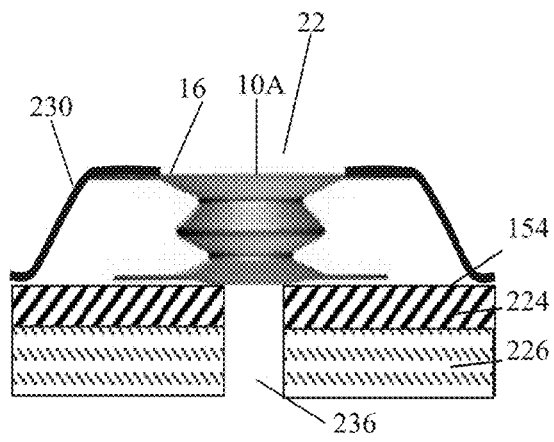
Figure 11B:
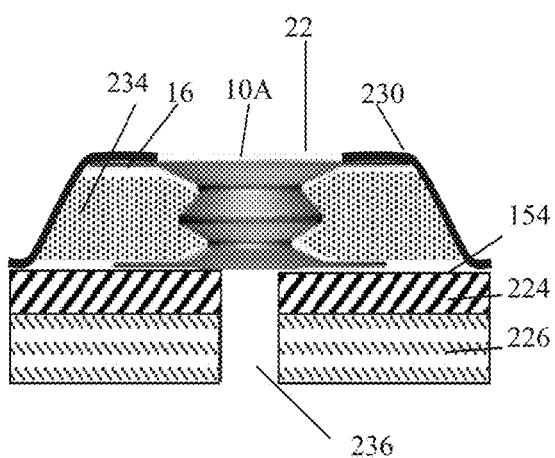

FIG. 11A shows a side view of device 10A adhered to skin 154 of a patient over opening 236 (e.g., wound, incision, or orifice) with an adhesive wound drape 230 placed on second flange 16 around second receptacle opening 22. Draped 230 may help hold device 10A in place relative to the skin of the patient as well as prevent exiting fluid through second receptacle opening 22 from contacting skin 154.

FIG. 11B shows a side view of device 10A adhered to skin 154 of a patient over opening 236 with adhesive wound drape 230 placed on second flange 16 around second receptacle opening 22. Included beneath drape 230 is a negative pressure dressing 234. A negative pressure (e.g., relative to the external atmosphere) may be applied to the negative pressure dressing 234 to draw adhesive wound drape 230 down toward skin 154, collapsing device 10A against skin 154 and holding device 10A in position around opening 236.

Figure 11C:
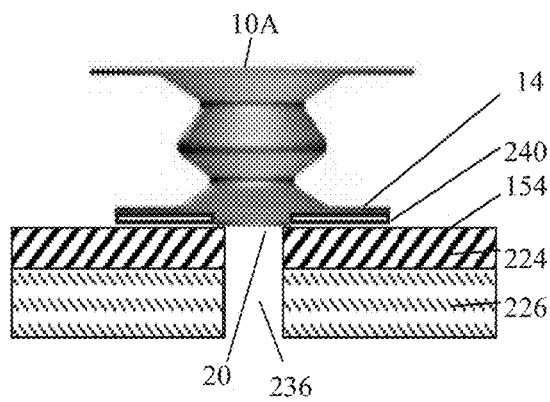

FIG. 11C shows a side view of device 10A adhered to skin 154 with hydrocolloid dressing or other skin adhesive 240 placed between first flange 14 to help secure first receptacle opening 20 to opening 236 and hold device 10A in position relative to skin 154. While device 10A is shown without skirt 26, in some examples, skirt 26 may be present and applied to opening 236.

Figure 11D:
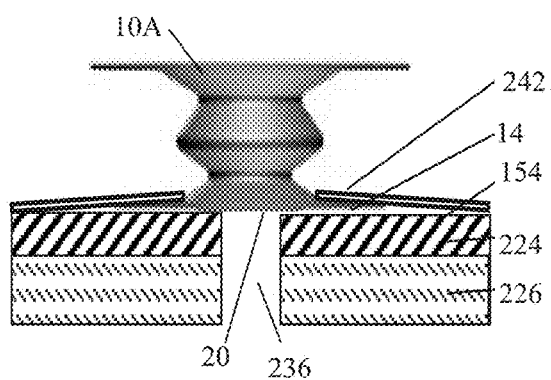

FIG. 11D shows a side view of device 10A adhered to skin 154 with adhesive wound drape 242 placed on first flange 14 such that first flange 14 is positioned between at least a portion of drape 242 and skin 154. Drape 242 may help hold device 10A in position relative to skin 154 while also allowing some movement of second flange 16 without stressing the adherence of drape 242.

Figure 11E:
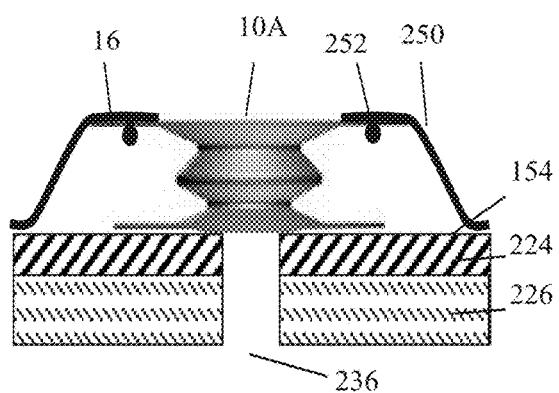

FIG. 11E shows a side view of device 10A being held to skin 154 over opening 236 with a wound dressing belt 250 mechanically fastened to second flange 16 by, for example, attachment hooks, loops, or buttons 252. Second flange 16 may include complementary structural features (e.g., apertures) configured to interact and mechanically engage with attachment hooks, loops, or buttons 252.

Figure 12A:
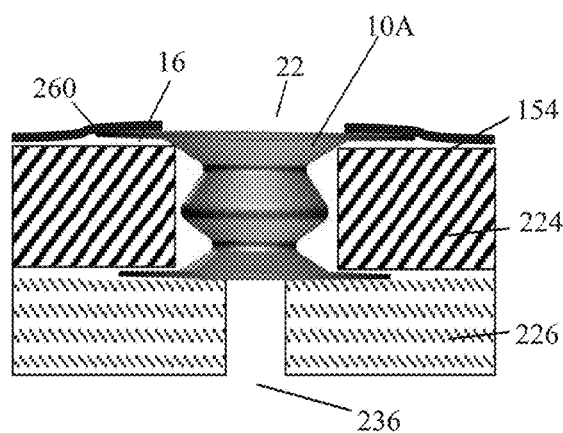
Figure 12B:
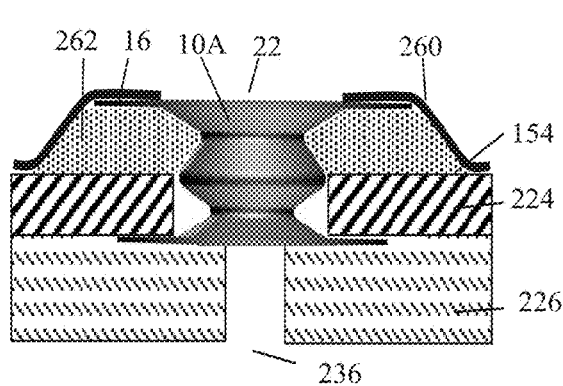
Figure 12C:
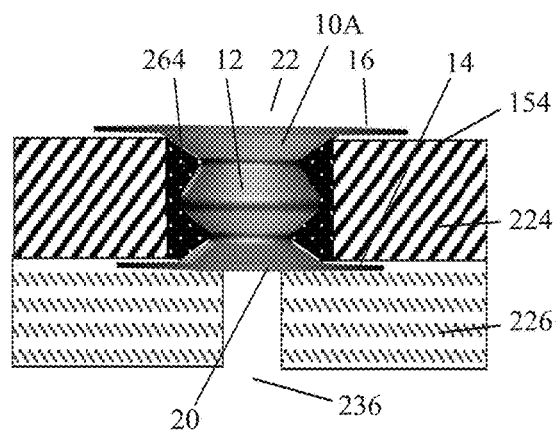

FIGS. 12A-12C show device 10A subcutaneously deployed between soft tissue layers 224 and muscle layers 226 in opening 236 and used in combination with one or more optional wound care devices. FIG. 12A shows a side view of device 10A placed subcutaneously and adhered to skin 154 with adhesive wound drape 260 placed on second flange 16 around second receptacle opening 22 to help hold device 10A in position around opening 236.

FIG. 12B shows a side view of device 10A placed subcutaneously and adhered to skin 154 with adhesive wound drape 260 placed second flange 16 similar to FIG. 12A but with the addition of negative pressure wound dressing 262 placed between skin 154 and second flange 16. As described above, a negative pressure may be applied to wound dressing 262 to draw adhesive wound drape 260 down toward skin 154, collapsing device 10A and holding it in position around opening 236.

FIG. 12C shows device 10A placed subcutaneously and adhered to skin 154 with hydrocolloid dressing or other wound sealant 264 placed around the exterior surface (e.g., surface in contact with subcutaneous layers 224 and 226) of fluid-containment receptacle 12 between first and second flanges 14 and 16 to hold device 10A in position in opening 236 and help create a fluid barrier between device 10A and the body of the patient.

Figure 13A:
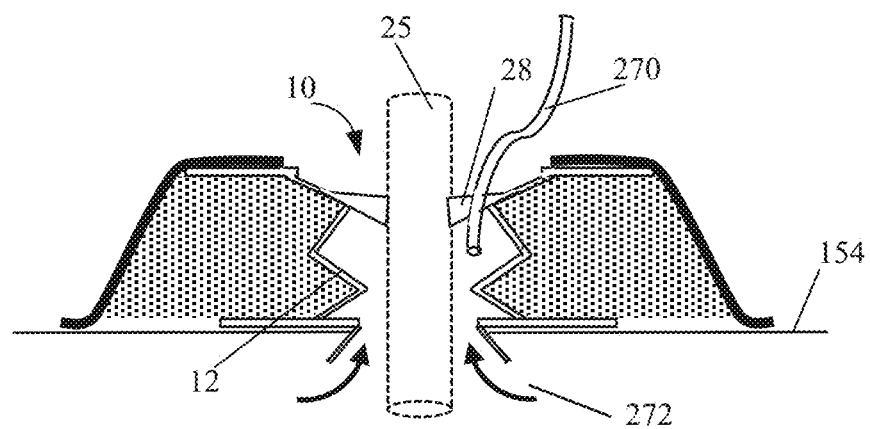
Figure 13B:
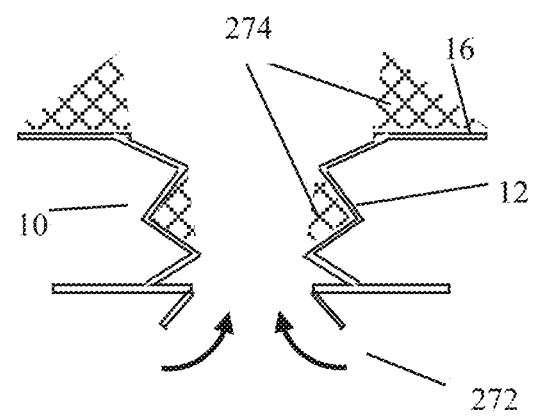

FIGS. 13A and 13B show addition examples for how device 10 may be used with other optional fluid management and wound care appliances. Any of the various options shown in FIGS. 13A and 13B may be used in any combination with any of the devices, device features, and fluid management systems described herein.

FIG. 13A shows a cross-sectional view of device 10 being used in combination with medical tube 25 and a suction tube 270. Suction tube 270 may be passed through second receptacle opening 22 into the inner volume of fluid-containment receptacle 12 to help transport fluid leakage 272 that passes between medical tube 25 and fluid-containment receptacle 12. Suction tube 270 may be used in combination with a wound care drape (e.g., wound care drape 230 of FIG. 12B) or other optional device.

FIG. 13B shows device 10 with absorbent dressing 274 placed inside fluid-containment receptacle 12 and on second flange 16 around the secondary receptacle opening 20. Dressing 280 may help capture leakage 272 that passes through the inner volume defined by fluid-containment receptacle 12. In some examples, dressing 274 may be packed into device 10 by a user or may be applied to device 10 at the point of manufacture.

According to an embodiment, a method for managing the passage of fluid through an opening in the body of a patient includes applying a fluid management device as described herein to the opening to form a fluid barrier against the body of the patient. In some examples, applying the fluid management device to the opening in the body of the patient includes positioning the device in the opening such that the first opening and the first flange contacts the body of the patient and forms a fluid barrier against the body of the patient. In some examples, the method includes introducing a medical tube through the opening in the body of the patient, where the fluid management device receives the medical tube. In embodiments, introducing the medical tube can include, for example, but is not limited to, inserting the medical tube into a stomach of a patient as part of a gastric feeding system, inserting the medical tube through a rectum of a patient as part of a fecal matter management system, and/or inserting the medical tube through a wound or incision in the body of the patient as part of a drainage incision system.

According to another embodiment, a medical kit includes a fluid management system as described herein for managing the passage of fluid through an opening in the body of a patient. The fluid management system includes a medical tube for introducing or removing a fluid through an opening in a body of a patient, and a fluid management device as described herein configured to be received over the medical tube and form a fluid barrier against the body of the patient. The medical kit may also include a set of instructions for using the fluid management system for managing the passage of fluid through an opening in the body of a patient. In some examples, the fluid management system is contained within a sterilized environment, such as, for example, within hermetically sealed packaging.

In some embodiments, the medical kit includes a set of instructions for applying the fluid management device to manage the passage of fluid through an opening in the body of a patient. The set of instructions can include instructions for instructing a user to introduce the medical tube through the opening in the body of the patient, and to apply the fluid management device to the opening in the body of the patient such that the first opening and the first flange contacts the body of the patient to form a fluid barrier against the body of the patient. For example, the set of instructions can include instructions for inserting the medical tube into a stomach of a patient as part of a gastric feeding system, instructions for inserting the medical tube through a rectum of a patient as part of a fecal matter management system, and/or instructions for inserting the medical tube through a wound or incision in the body of the patient as part of a drainage incision system.

Persons of ordinary skill in the relevant arts will recognize that the subject matter hereof may comprise fewer features than illustrated in any individual example described above. The examples described herein are not meant to be an exhaustive presentation of the ways in which the various features of the subject matter hereof may be combined. Accordingly, the examples are not mutually exclusive combinations of features; rather, the various examples can comprise a combination of different individual features selected from different individual examples, as understood by persons of ordinary skill in the art. Moreover, elements described with respect to one example can be implemented in other examples even when not described in such examples unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

What is claimed is:

1. A device for managing the passage of fluid through an opening in the body of a patient, the device comprising:
    a unitary fluid-containment receptacle comprising
        a collapsible sidewall that extends along a longitudinal axis, the fluid-containment receptacle having structure defining a first receptacle opening and a second receptacle opening positioned at opposite ends of the sidewall, the fluid-containment receptacle configured to collapse from a first height to a second height less than the first height when subject to axial force applied to the device along the longitudinal axis,
        a first flange extending radially outward from the sidewall and positioned at or adjacent to the first receptacle opening,
        a second flange extending radially outward from the sidewall at or adjacent to the second receptacle opening, and
        a flexible skirt longitudinally depending from sidewall below the first flange,
    wherein the device is configured to be applied around the opening in the body of the patient such that the first flange interfaces with the body of the patient and the flexible skirt forms a fluid barrier around the opening, wherein the second flange is configured to interface with an absorbent dressing, a pouch appliance, or both, and wherein the sidewall is configured to compress along the longitudinal axis from the first height to the second height thereby forcing the second flange proximate the first flange when the axial force is applied to form a fluid barrier against the body of the patient.

2. The device of claim 1, wherein the fluid-containment receptacle is configured to receive a medical tube inserted through the device along the longitudinal axis, wherein the device is configured to resist axial movement of the medical tube once the medical tube is inserted through the device.

3. The device of claim 2, wherein the fluid-containment receptacle further comprises at least one tube retainer that extends radially inward from the sidewall towards the longitudinal axis, wherein the at least one tube retainer is configured to contact an inserted medical tube and limit axial motion of the medical tube through the device.

4. The device of claim 3, wherein the at least one tube retainer is configured to form a non-fluidic seal with the received medical tube to allow for the passage of fluid between the fluid-containment receptacle and the medical tube.

5. The device of claim 1, wherein the fluid-containment receptacle further comprises a retaining sleeve that defines a tubular shape that extends along the longitudinal axis, the retaining sleeve configured to receive an inserted medical tube and limit axial motion of the medical tube through the device.

6. The device of claim 5, wherein the retaining sleeve defines a slot that extends in the direction of the longitudinal axis.

7. The device of claim 5, wherein the retaining sleeve comprises an integral fastener configured to secure the retaining sleeve to the received medical tube.

8. The device of claim 5, wherein the sidewall defines a tapered section that radially tapers inward from the second flange to the retaining sleeve.

9. The device of claim 1, wherein the sidewall defines a plurality of pleats configured to allow the fluid-containment receptacle to collapse along the longitudinal axis from the first height to the second height.

10. The device of claim 1, wherein the sidewall defines a plurality of ridges configured to allow the fluid-containment receptacle to collapse along the longitudinal axis from the first height to the second height.

11. The device of claim 1, wherein at least one of the first flange and the second flange include an adhesive material or adhesive wound drape attached to an outer surface of the first flange or the second flange.

12. The device of claim 1, wherein at least one of the fluid-containment receptacle and the second flange include an absorbent dressing material or a pouch appliance attached on a surface thereof, configured to capture leaked fluid that passes through the fluid-containment receptacle.

13. The device of claim 1, wherein the device comprises a configurable material that can be cut to size using a pair of scissors.

14. A fluid management system comprising:
    a medical tube for introducing or removing a fluid through an opening in a body of a patient;
    a fluid management device configured to be received over the medical tube and form a fluid barrier against the body of the patient, the fluid management device comprising:
        a unitary fluid-containment receptacle comprising a collapsible sidewall that extends along a longitudinal axis, the fluid-containment receptacle having a first receptacle opening and a second receptacle opening positioned at opposite ends of the sidewall, the fluid-containment receptacle configured to collapse from a first height to a second height less than the first height when subject to axial force applied to the device along the longitudinal axis;
a first flange extending radially outward from the sidewall and positioned at or adjacent to the first receptacle opening;
a second flange extending radially outward from the sidewall at or adjacent to the second receptacle opening; and
a flexible skirt longitudinally depending from sidewall below the first flange,
wherein the device is configured to be applied around the opening in the body of the patient such that the first flange interfaces with the body of the patient and the flexible skirt extends forms a fluid barrier around the opening, wherein the second flange is configured to interface with an absorbent dressing, a pouch appliance, or both, and wherein the sidewall is configured to compress along the longitudinal axis from the first height to the second height thereby forcing the second flange proximate the first flange when the axial force is applied to form a fluid barrier against the body of the patient.

15. The fluid management system of claim 14, wherein the fluid-containment receptacle further comprises at least one tube retainer that extends radially inward from the sidewall towards the longitudinal axis, wherein the at least one tube retainer is configured to contact the medical tube and limit axial motion of the medical tube through the device.

16. The fluid management system of claim 14, wherein the fluid-containment receptacle further comprises a retaining sleeve that defines a tubular shape that extends along the longitudinal axis, the retaining sleeve configured to be secured to the medical tube and limit axial motion of the medical tube through the device.

17. The fluid management system of claim 14, wherein the sidewall defines a plurality of pleats configured to allow the fluid-containment receptacle to collapse along the longitudinal axis from the first height to the second height.

18. The fluid management system of claim 14, wherein fluid management system is a fecal matter management system, a gastric feeding system, or a drainage incision system.

* * * * *